US011006948B2

(12) United States Patent
Majors et al.

(10) Patent No.: US 11,006,948 B2
(45) Date of Patent: May 18, 2021

(54) SURGICAL STAPLE AND INSTRUMENT FOR HOLDING AND IMPLANTING THE SURGICAL STAPLE

(71) Applicant: Biedermann Technologies GmbH & Co. KG, Donaueschingen (DE)

(72) Inventors: Benjamin Majors, Englewood, CO (US); Achim Zipse, Baden-Baden (DE); Gael Dreher, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 268 days.

(21) Appl. No.: 15/975,047

(22) Filed: May 9, 2018

(65) Prior Publication Data
US 2019/0000451 A1     Jan. 3, 2019

Related U.S. Application Data

(60) Provisional application No. 62/526,147, filed on Jun. 28, 2017.

(51) Int. Cl.
*A61B 17/064*     (2006.01)
*A61B 17/068*     (2006.01)
(Continued)

(52) U.S. Cl.
CPC ...... *A61B 17/0642* (2013.01); *A61B 17/0682* (2013.01); *A61B 17/10* (2013.01); *A61B 17/17* (2013.01); *A61B 2017/0645* (2013.01)

(58) Field of Classification Search
CPC .. A61B 17/0642–0644; A61B 17/0682; A61B 17/10; A61B 17/17; A61B 17/068;
(Continued)

(56) References Cited

U.S. PATENT DOCUMENTS 503,271 A * 8/1893 Ortloff ............ B27F 7/21
                                            227/88
3,095,393 A * 6/1963 Matt ............... C08L 67/06
                                          524/598
(Continued)

FOREIGN PATENT DOCUMENTS

DE     4110123 A1    10/1992
DE     19821680 C1    8/1999
(Continued)

OTHER PUBLICATIONS

European Search Report and Search Opinion for EP 15168542.7 mailed by the EPO dated Nov. 9, 2015 (11 pages).
(Continued)

*Primary Examiner* — Jessica Weiss
(74) *Attorney, Agent, or Firm* — Gordon & Jacobson, P.C.

(57) ABSTRACT

Devices, instruments, assemblies, and systems for holding and inserting staples and staples for compressing bones or bone fragments. The staple insertion assembly including a staple holder and a staple. The staple holder including a first and second end with a gripping portion at the first end, at least one slot extending from second end toward first end, and a receiving portion at the second end. The receiving portion with at least one staple contact portion, a first recessed region positioned adjacent to the at least one staple contact portion on a first side and a second recessed region positioned adjacent to the at least one staple contact portion on a second side, and a first engagement member positioned adjacent to the first recessed region and a second engagement member positioned adjacent to the second recessed region. Methods for using the assemblies to compress bones or bone fragments are also disclosed.

32 Claims, 32 Drawing Sheets

(51) Int. Cl.
*A61B 17/17* (2006.01)
*A61B 17/10* (2006.01)

(58) Field of Classification Search
CPC ........ A61B 17/072; A61B 2017/07214; A61B 2017/07221; A61B 2017/07228; A61B 2017/07235; A61B 2017/07242; A61B 2017/0645–0646
USPC ............ 606/219, 138–139; 227/175.1–182.1
See application file for complete search history.

(56) References Cited

U.S. PATENT DOCUMENTS

| | | | |
|---|---|---|---|
| 4,263,903 A | 4/1981 | Griggs | |
| 4,438,769 A * | 3/1984 | Pratt | A61B 17/0642 227/147 |
| 4,570,623 A | 2/1986 | Ellison et al. | |
| 5,454,814 A | 10/1995 | Comte | |
| 5,634,926 A | 6/1997 | Jobe | |
| 5,785,713 A | 7/1998 | Jobe | |
| 6,325,805 B1 | 12/2001 | Ogilvie et al. | |
| 6,908,467 B2 | 6/2005 | Ip et al. | |
| 7,618,441 B2 | 11/2009 | Groiso | |
| D676,962 S * | 2/2013 | Cheney | 227/88 |
| 8,596,514 B2 | 12/2013 | Miller et al. | |
| 9,675,344 B2 * | 6/2017 | Combrowski | A61B 17/0401 |
| 2002/0111641 A1 | 8/2002 | Peterson et al. | |
| 2012/0024937 A1 * | 2/2012 | Allen | A61B 17/0642 227/181.1 |
| 2012/0228355 A1 * | 9/2012 | Combrowski | A61B 17/1285 227/175.1 |
| 2013/0026206 A1 | 1/2013 | Fox | |
| 2013/0231667 A1 | 9/2013 | Taylor et al. | |
| 2014/0097228 A1 | 4/2014 | Taylor et al. | |
| 2014/0277516 A1 | 9/2014 | Miller et al. | |
| 2014/0358187 A1 * | 12/2014 | Taber | A61B 17/0682 606/86 R |
| 2016/0199060 A1 | 7/2016 | Morgan et al. | |
| 2016/0338697 A1 | 11/2016 | Biedermann et al. | |
| 2017/0000482 A1 * | 1/2017 | Averous | A61B 17/0642 |
| 2017/0196604 A1 * | 7/2017 | Hartdegen | A61B 17/8085 |
| 2019/0069892 A1 | 3/2019 | Biedermann et al. | |

FOREIGN PATENT DOCUMENTS

| | | |
|---|---|---|
| EP | 0503271 A2 | 9/1992 |
| EP | 3095393 A1 | 11/2016 |
| FR | 2725126 A1 | 4/1996 |
| FR | 2926453 A1 | 7/2009 |
| FR | 2999069 A1 | 6/2014 |
| GB | 2471648 B | 1/2011 |
| WO | WO92/17122 A2 | 10/1992 |
| WO | WO 2010/004602 A1 | 1/2010 |
| WO | WO 2016/007624 A1 | 1/2016 |
| WO | WO 2016/154417 A1 | 9/2016 |

OTHER PUBLICATIONS

Extended European Search Report of Application No. 18179393.6 dated Nov. 19, 2018.

* cited by examiner

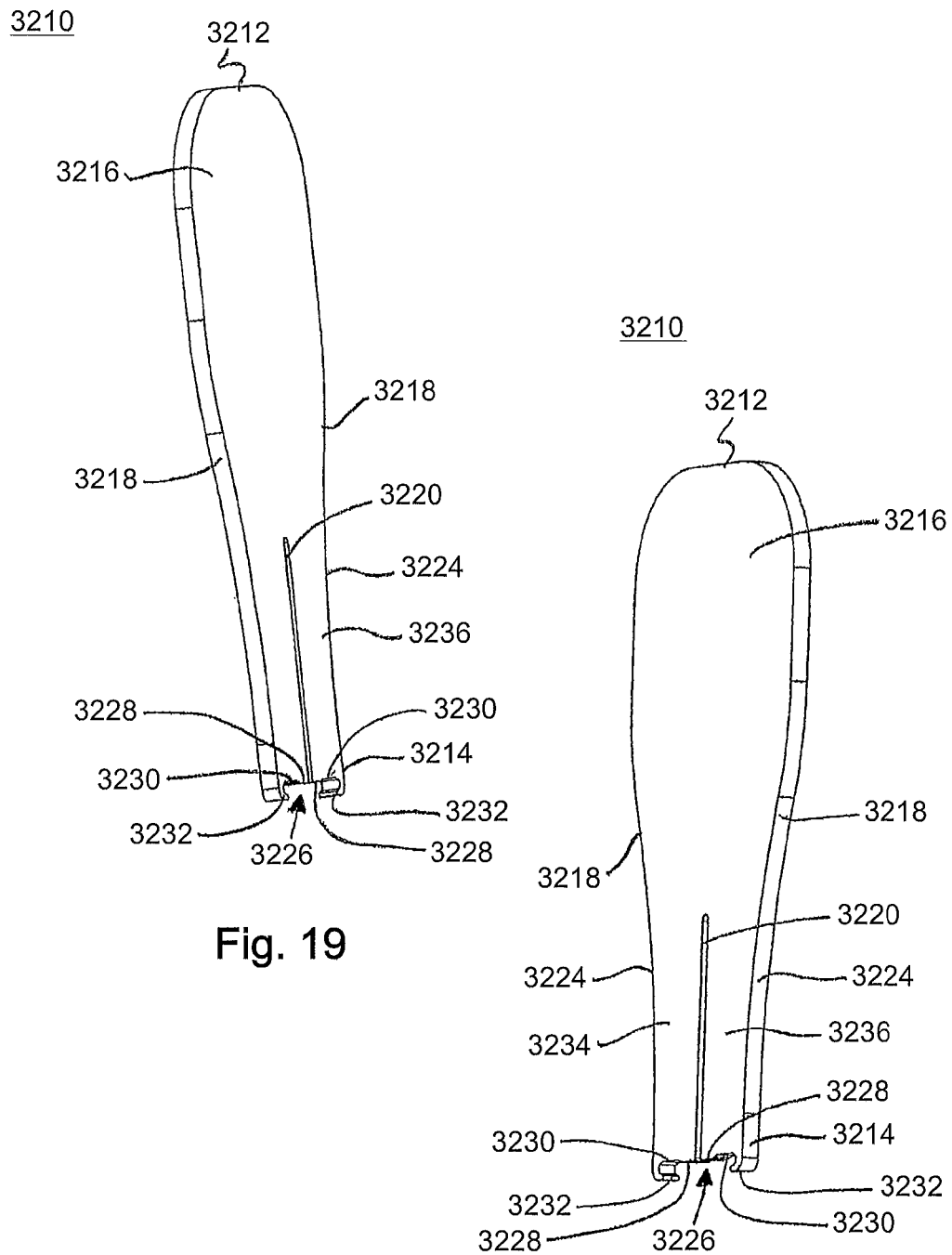

SURGICAL STAPLE AND INSTRUMENT FOR HOLDING AND IMPLANTING THE SURGICAL STAPLE

CROSS-REFERENCE TO RELATED APPLICATIONS

This application claims benefit of U.S. Provisional Ser. No. 62/526,147, filed Jun. 28, 2017, which is hereby incorporated by reference herein in its entirety.

This application is related to U.S. application Ser. No. 15/161,124, filed on May 20, 2016, which claims priority benefit of U.S. Provisional Patent Application No. 62/164,402, filed on May 20, 2015, and claims priority from European Patent Application EP 15168542.7, filed on May 20, 2015, the contents of which are hereby incorporated by reference in their entireties.

FIELD OF INVENTION

The present invention relates generally to surgical staples used for compressing bones or bone fragments. More specifically, the invention relates to surgical staples including a first leg for anchoring in a first bone or bone fragment, a second leg for anchoring in a second bone or bone fragment, and a bridge connecting the first leg and the second leg. The invention also relates to an instrument for holding and implanting surgical staples.

BACKGROUND

Surgical staples are used to treat angular deformations, fractures particularly with respect to the extremities, subluxation, dislocation, arthritis, or other issues that may occur with regard to bones of the human body. The staples are attached to respective bones or bone fragments to fuse the bones or bone fragments together while exerting a compressive force on them. Staples are advantageous over other fusion techniques such as plates, for example, in view of their compactness and flexibility.

SUMMARY

The present invention is directed toward devices, assemblies and methods for holding and inserting staples and staples for compressing bones or bone fragments.

In one aspect of the present invention provided herein, is a staple insertion assembly. The staple insertion assembly including a staple holder with a first end and a second end and a staple. The staple holder including a gripping portion at the first end, at least one slot extending from the second end toward the first end, and a receiving portion at the second end. The receiving portion including at least one staple contact portion, a first recessed region positioned adjacent to the at least one staple contact portion on a first side and a second recessed region positioned adjacent to the at least one staple contact portion on a second side, and a first engagement member positioned adjacent to the first recessed region and a second engagement member positioned adjacent to the second recessed region.

In another aspect of the present invention provided herein, is a staple holder. The staple holder including a gripping portion at a first end, at least one slot extending from a second end toward the first end, and a receiving portion at the second end. The receiving portion including at least one staple contact portion, a first recessed region positioned adjacent to the at least one staple contact portion on a first side and a second recessed region positioned adjacent to the at least one staple contact portion on a second side, and a first engagement member positioned adjacent to the first recessed region and a second engagement member positioned adjacent to the second recessed region.

These and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 19 is a first side perspective view of the staple holder of FIG. 17, in accordance with an aspect of the present invention;

FIG. 20 is a second side perspective view of the staple holder of FIG. 17, in accordance with an aspect of the present invention;

DETAILED DESCRIPTION

Figure 1:
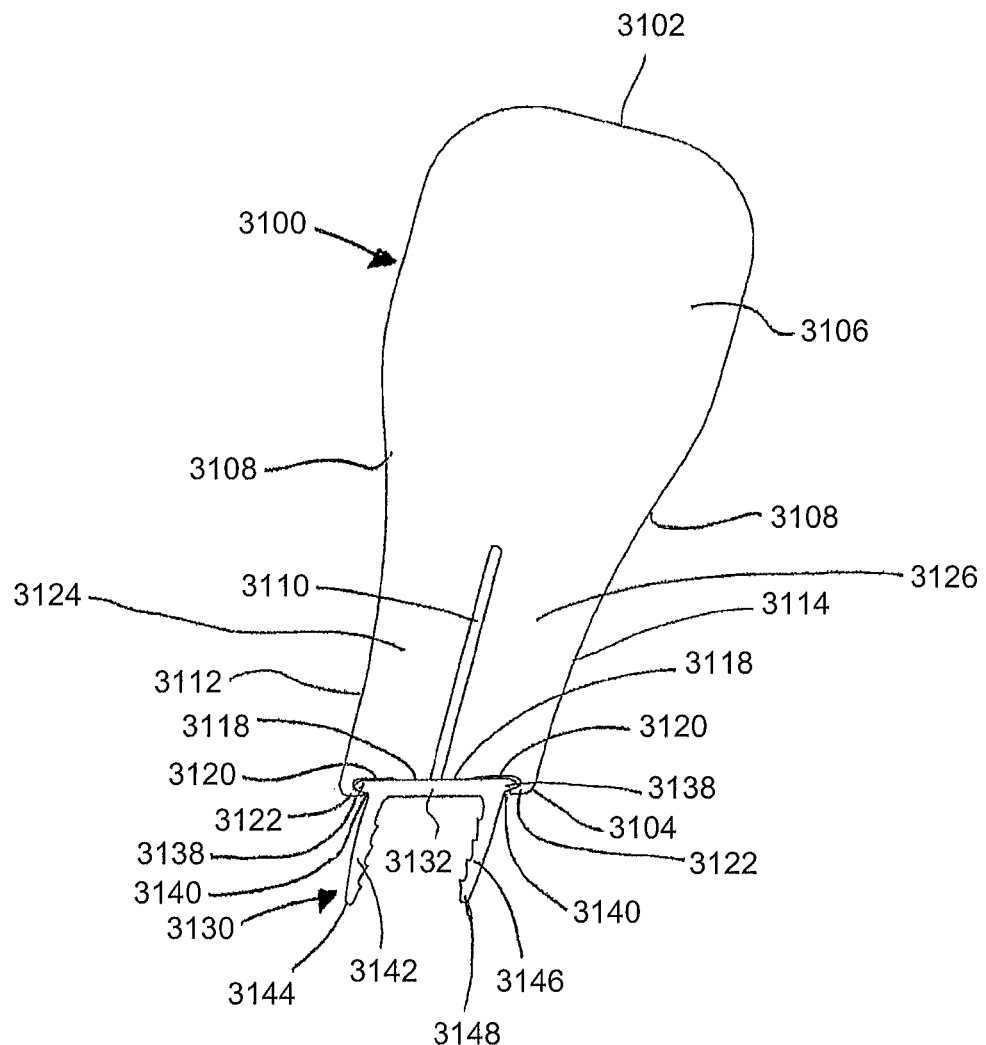
FIG. 1 is a front view of an embodiment of a staple insertion assembly, in accordance with an aspect of the present invention.

Generally stated, disclosed herein are devices, instruments, and systems for holding and inserting surgical staples and surgical staples for compressing bones or bone fragments. Further, methods for using the devices, instruments, systems, and surgical staples to compress bones or bone fragments are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the right foot may be mirrored so that they likewise function with the left foot. Further, the implants, devices, instrumentation and methods, and the aspects, components, features and the like thereof, disclosed herein are described with respect to the foot for brevity purposes, but it should be understood that the implants, devices, instrumentation and methods may be used with other bones of the body having similar structures.

Figure 29:
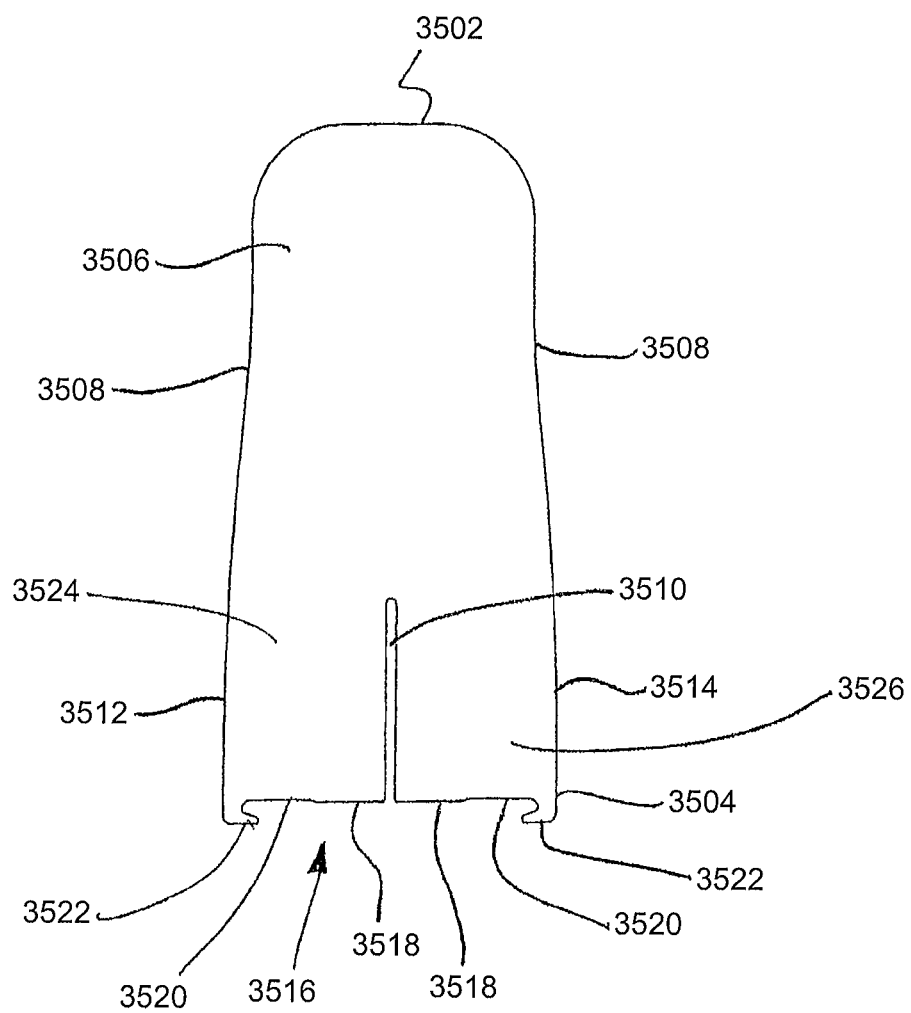
FIG. 29 is a front view of another embodiment of a staple holder, in accordance with an aspect of the present invention.
Figure 30:
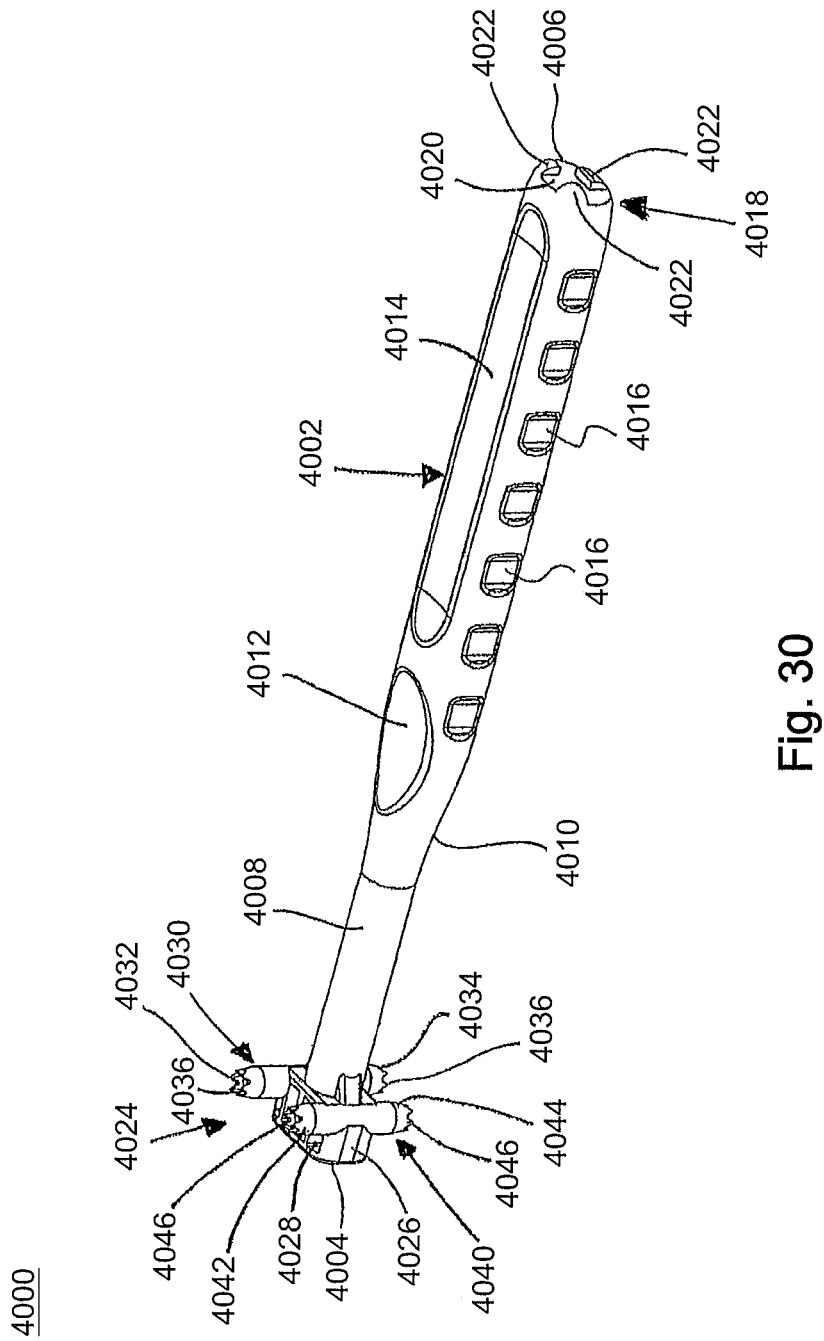
FIG. 30 is a first perspective view of a staple insertion instrument, in accordance with an aspect of the present invention.
Figure 31:
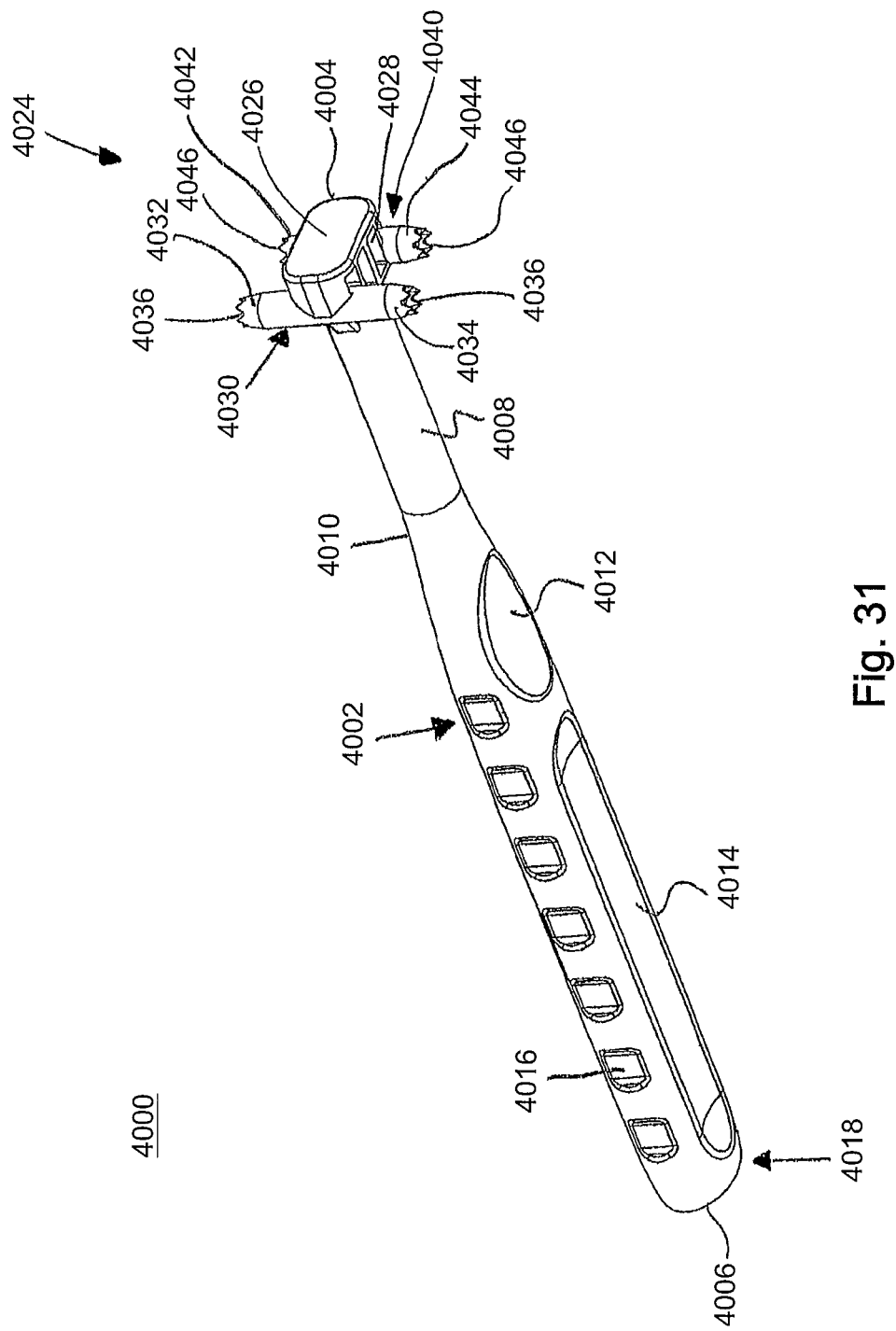
FIG. 31 is a second perspective view of the staple insertion instrument of FIG. 30, in accordance with an aspect of the present invention.
Figure 32:
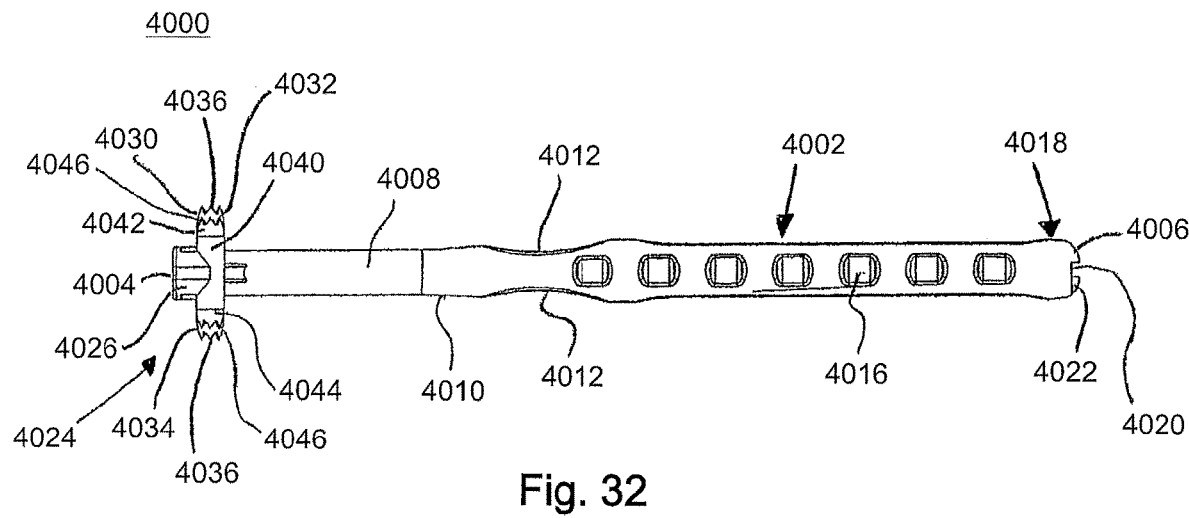
FIG. 32 is a first side view of the staple insertion instrument of FIG. 30, in accordance with an aspect of the present invention.
Figure 33:
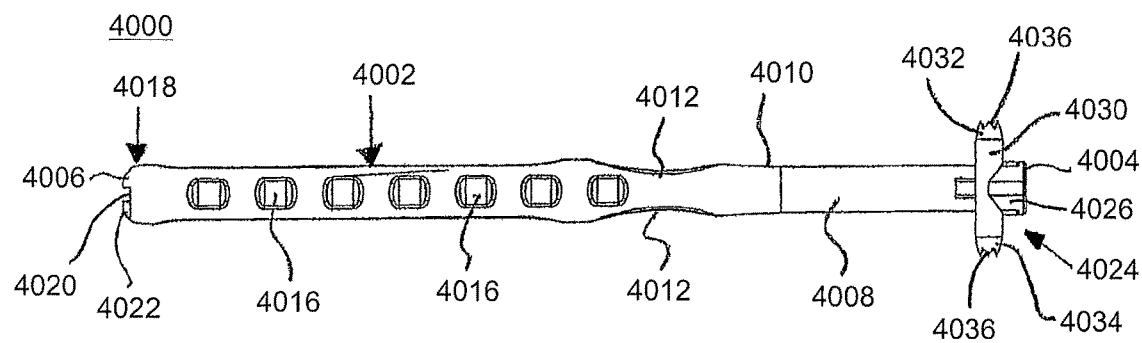
FIG. 33 is a second side view of the staple insertion instrument of FIG. 30, in accordance with an aspect of the present invention.
Figure 34:
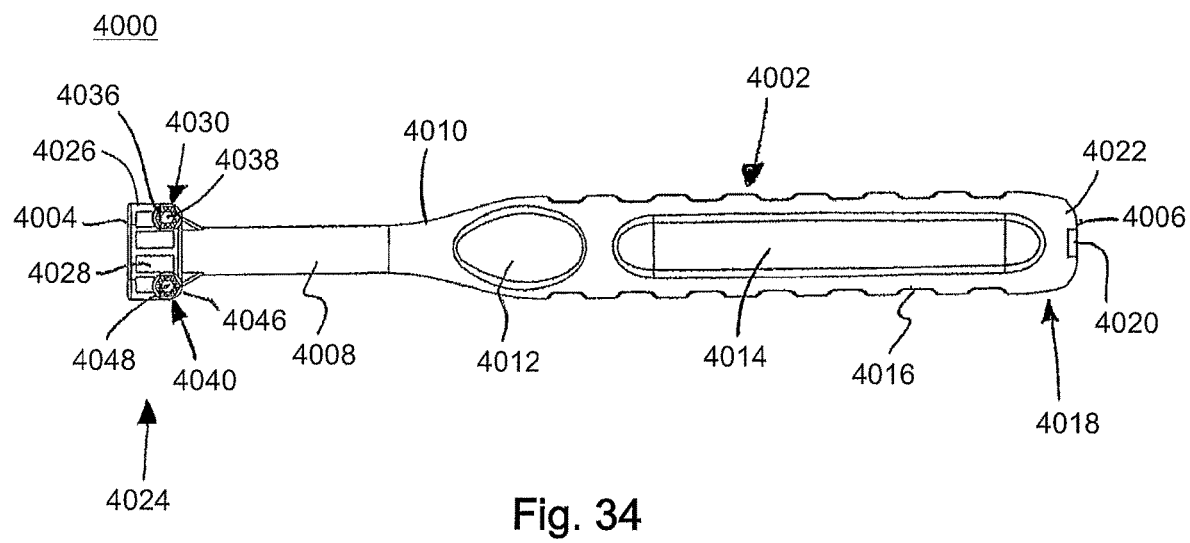
FIG. 34 is a top view of the staple insertion instrument of FIG. 30, in accordance with an aspect of the present invention.
Figure 35:
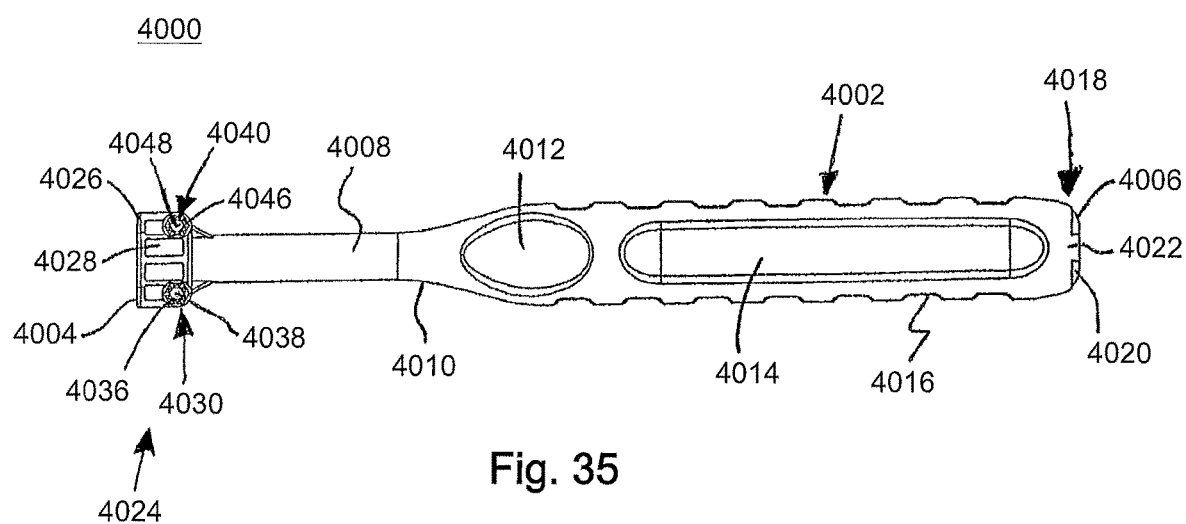
FIG. 35 is a bottom view of the staple insertion instrument of FIG. 30, in accordance with an aspect of the present invention.
Figure 36:
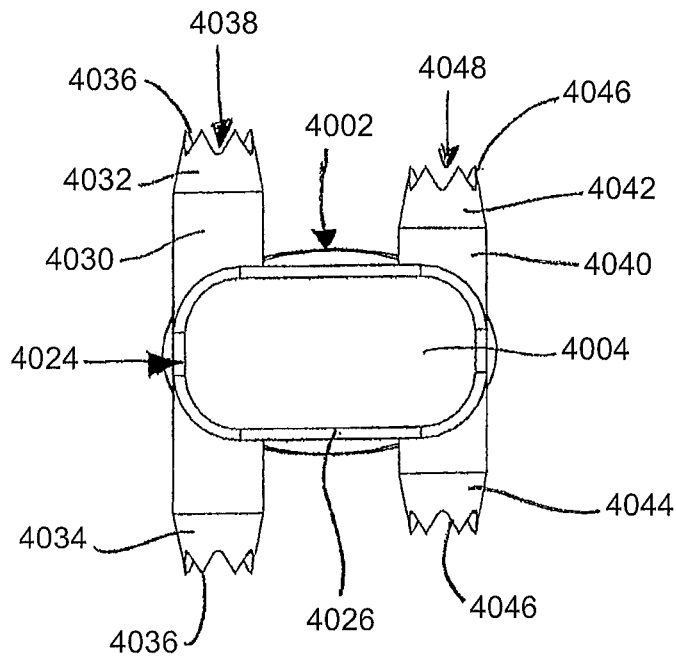
FIG. 36 is a first end view of the staple insertion instrument of FIG. 30, in accordance with an aspect of the present invention.
Figure 37:
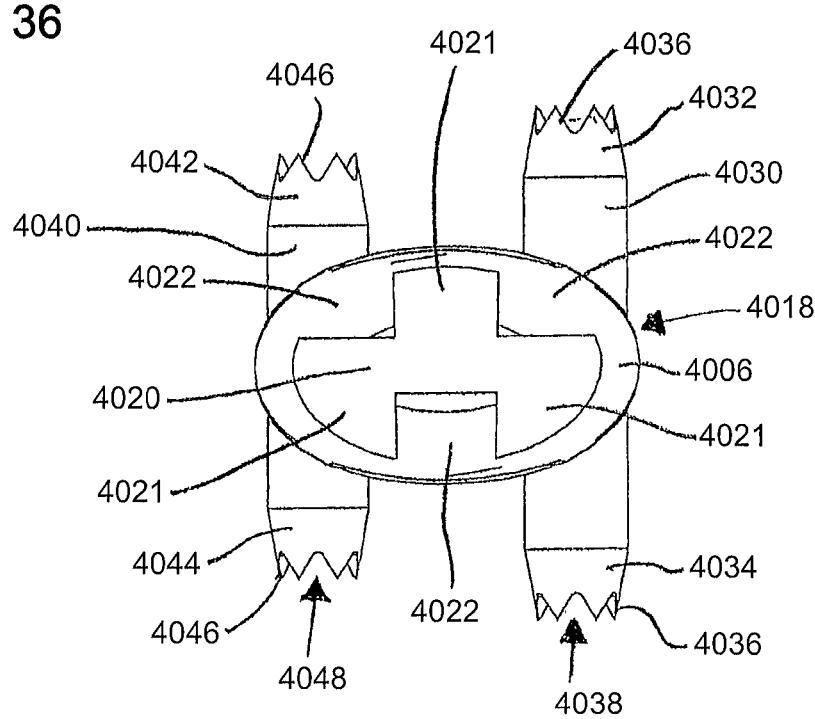
FIG. 37 is a second end view of the staple insertion instrument of FIG. 30, in accordance with an aspect of the present invention.
Figure 38:
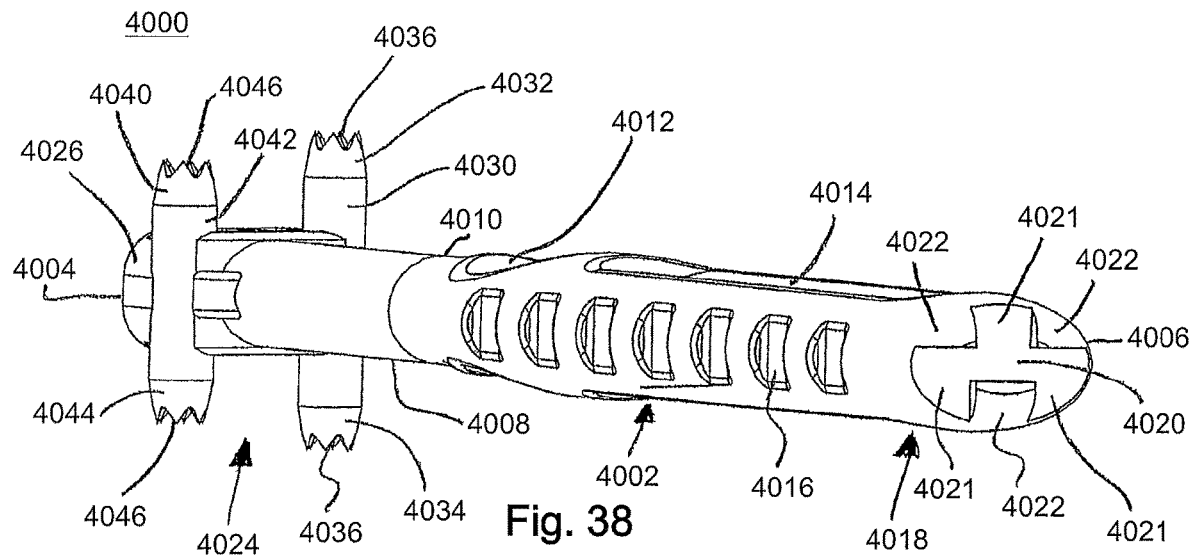
FIG. 38 is a side perspective view of the staple insertion instrument of FIG. 30, in accordance with an aspect of the present invention.

Referring to the drawings, wherein like reference numerals are used to indicate like or analogous components throughout the several views, and with particular reference to FIGS. 1-29, there are illustrated alternative embodiments of staple holders 3100, 3210, 3300, 3400, 3500 and staples 3130, 3240. An angled staple insertion assembly 3000 is shown in FIGS. 29 and 30. The angled staple insertion assembly 3000 includes a staple holder 3100 and a staple 3130. The staple 3130 is received within a second end 3104 of the staple holder 3100 for insertion into a patient. The holder 3100 may be used for final placement of the staple 3130, pre-compression of the surgical site if desired, release of energy within the staple 3130 for compression and in-vivo fixation.

The staple holder or body 3100, as shown in FIGS. 2-9, includes a first end 3102 and a second end 3104. The first end 3102 includes a gripping portion or handle portion 3106 for grasping during insertion of the staple 3130 into a patient. The gripping portion 3106 may extend from the first end 3102 to approximately a mid-point of the holder 3100 where the holder 3100 has curved or tapered sides 3108. The holder 3100 tapers from the curved sides 3108 toward the second end 3104. The holder 3100 may also optionally include, for example, a channel or slot 3110 extending from the second end 3104 into the body 3100 toward the first end 3102. The length of the slot 3110 may vary, for example, the slot 3110 may extend a given percentage of the length of the holder 3100. In an embodiment, the length of the slot 3110 may be, for example, approximately 23% to 58% of the height of the holder 3100, more specifically, approximately 38.5% to 38.8% of the height of the holder 3100. As shown in the depicted embodiment, the slot 3110 may be positioned, for example, at a center of the second end 3104. It is also contemplated that the slot 3110 may be offset from the center of the second end 3104. Further, it is also contemplated that the slot 3110 may be, for example, more than one slot 3110, specifically, if the holder 3100 receives, for example, a stepped staple (not shown). The slot 3110 may separate a portion of the holder 3100 to form a first member 3124 and a second member 3126 extending from the second end 3104 of the holder 3100. The first member 3124 may be, for example, a mirror image of the second member 3126. The slot 3110 provides a degree of flexibility to the holder 3100 such that when the gripping portion 3106 is rotated, flexed, or bent relative to the second end 3104 of the holder, the staple retained in the holder, and energy stored in the holder, can be released.

Figure 3:
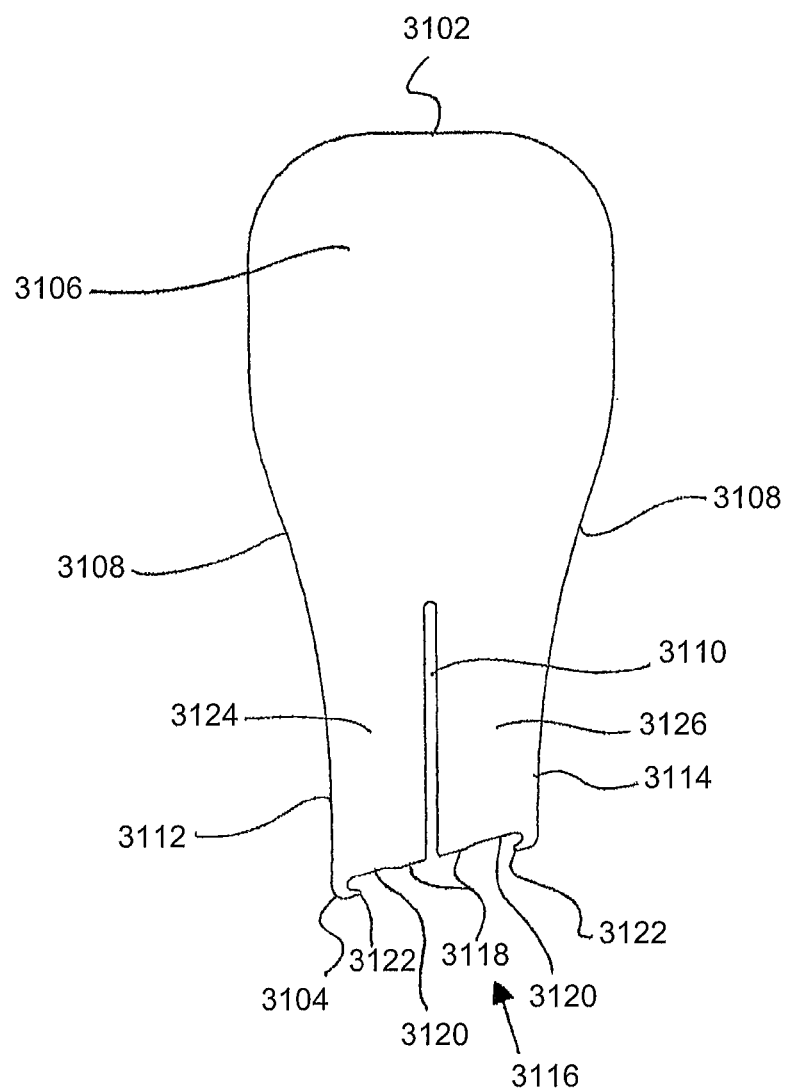
FIG. 3 is a front view of the staple holder of the staple insertion assembly of FIG. 1, in accordance with an aspect of the present invention.
Figure 4:
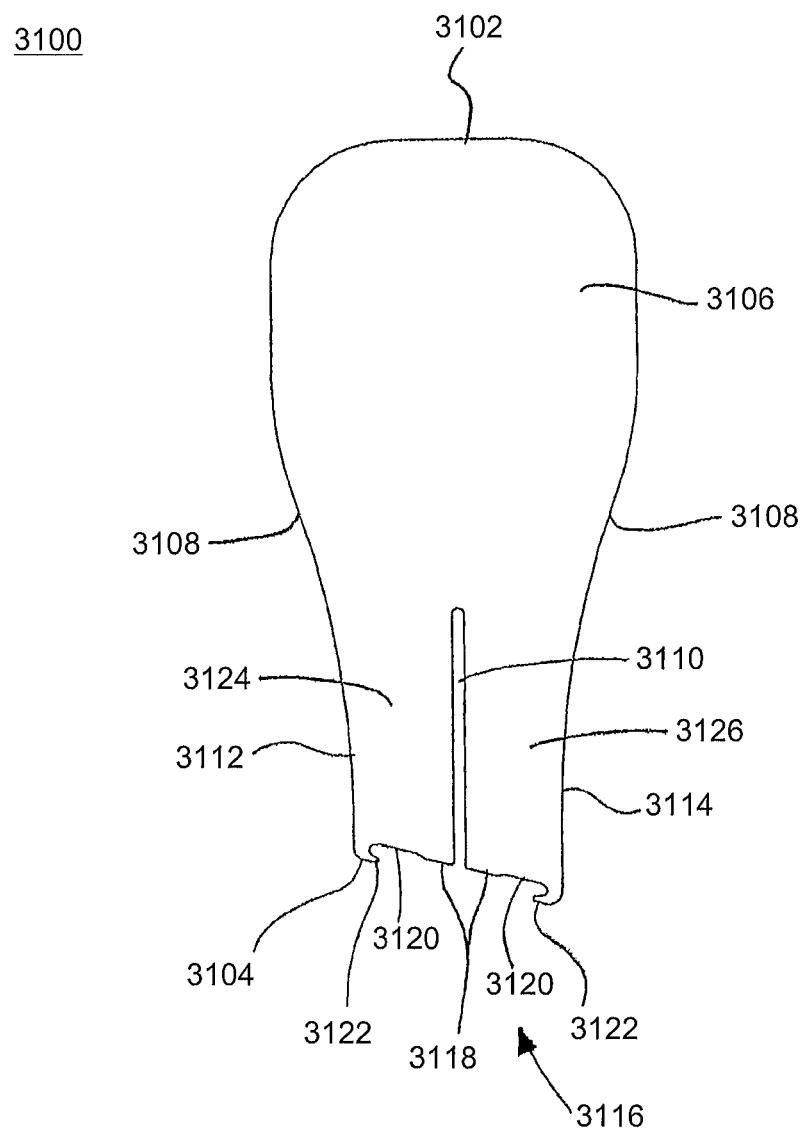
FIG. 4 is a rear view of the staple holder of FIG. 3, in accordance with an aspect of the present invention.
Figure 5:
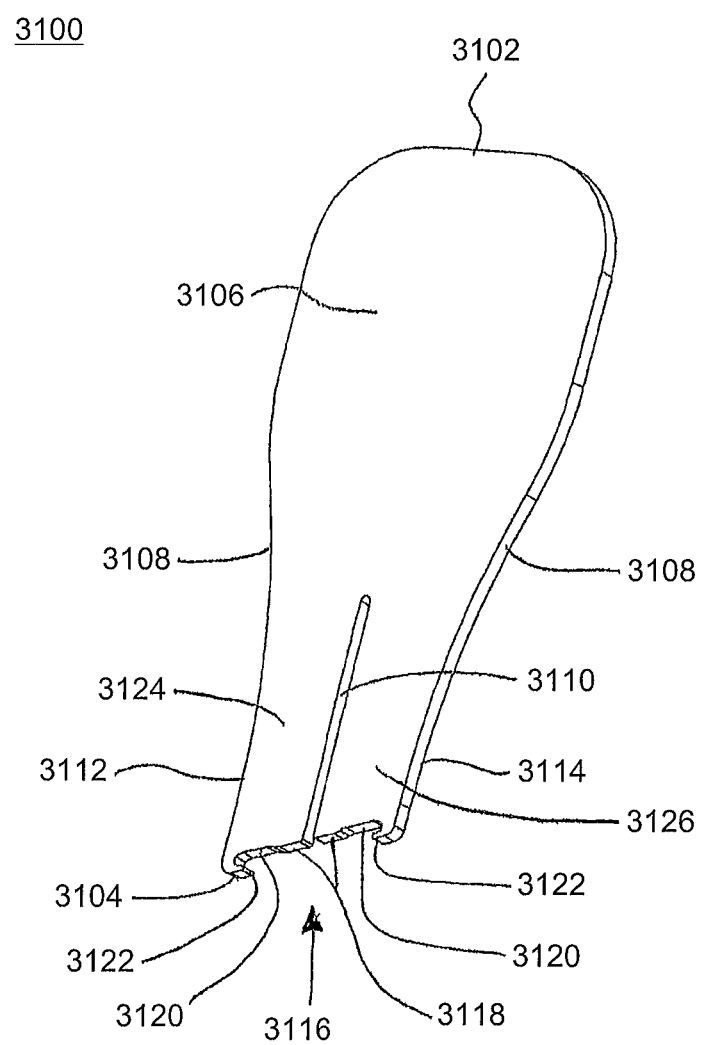
FIG. 5 is a front perspective view of the staple holder of FIG. 3, in accordance with an aspect of the present invention.
Figure 6:
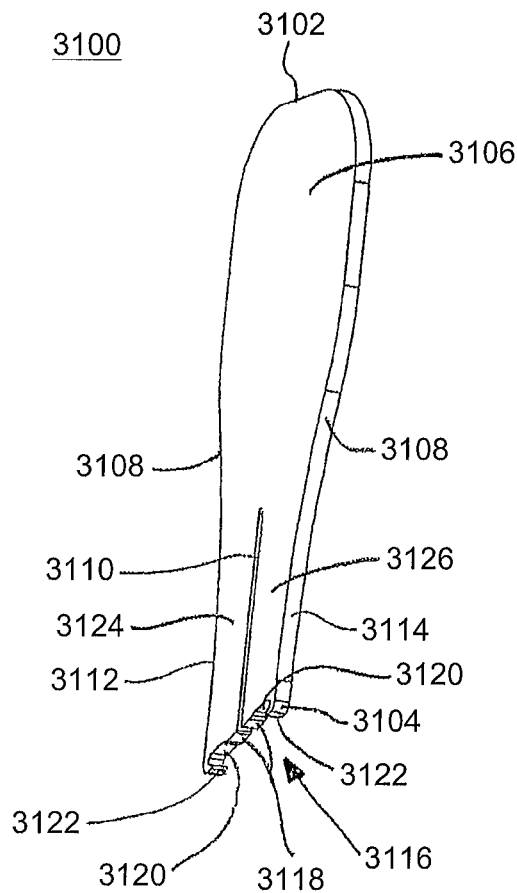
FIG. 6 is a first side perspective view of the staple holder of FIG. 3, in accordance with an aspect of the present invention.
Figure 7:
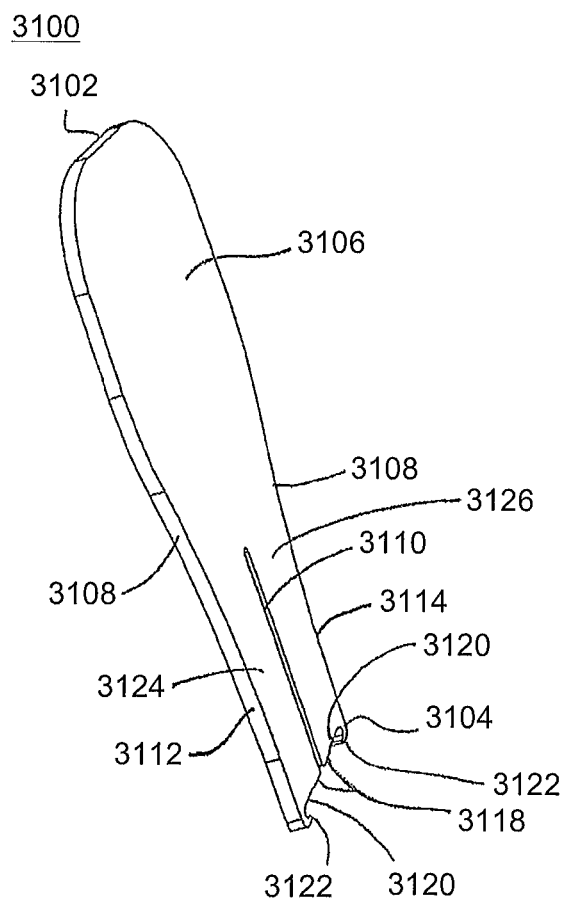
FIG. 7 is a second side perspective view of the staple holder of FIG. 3, in accordance with an aspect of the present invention.
Figure 8:
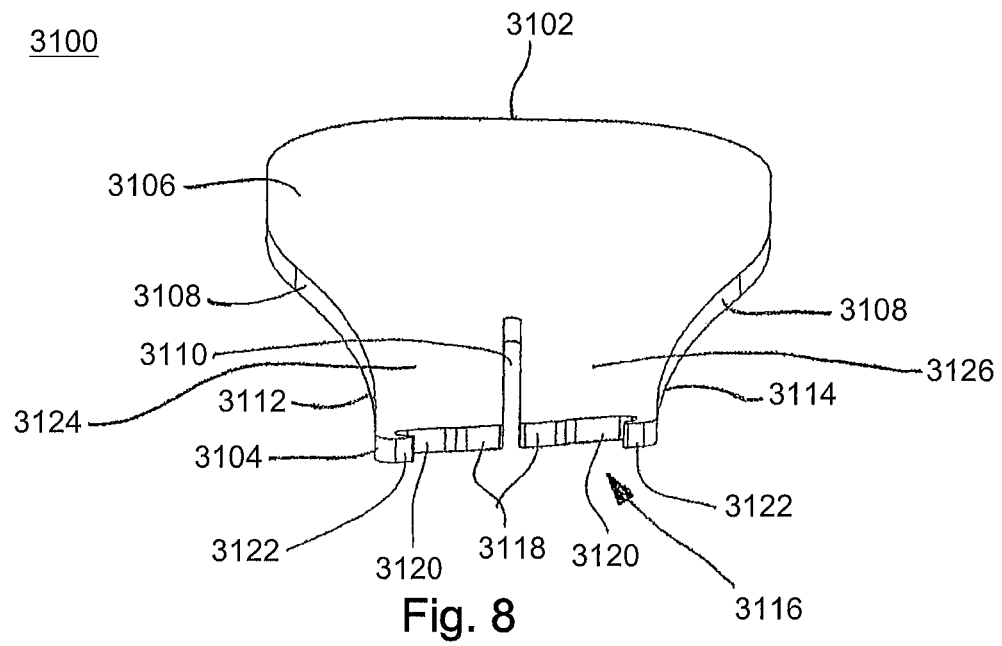
FIG. 8 is a first end perspective view of the staple holder of FIG. 3, in accordance with an aspect of the present invention.
Figure 9:
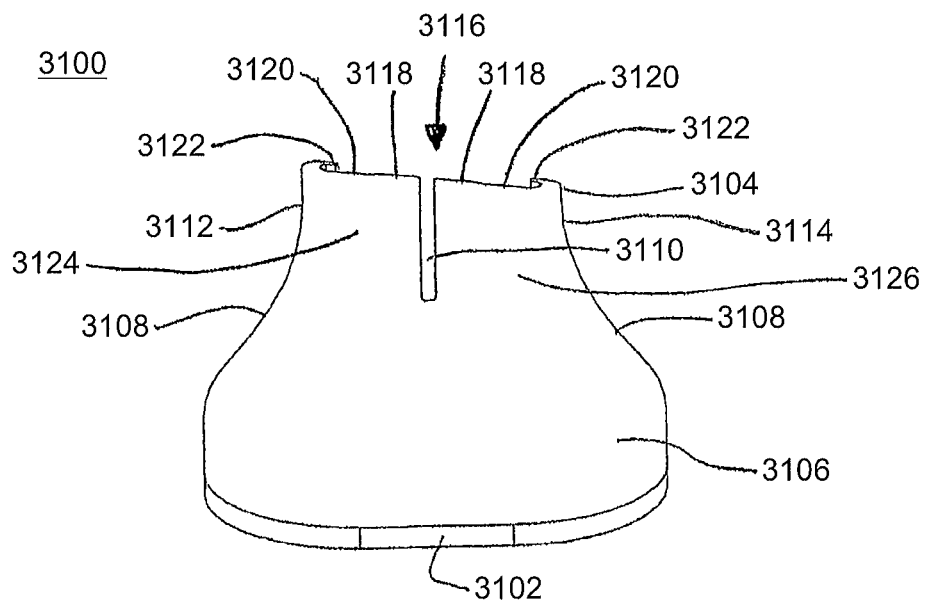
FIG. 9 is a second end perspective view of the staple holder of FIG. 3, in accordance with an aspect of the present invention.
Figure 10:
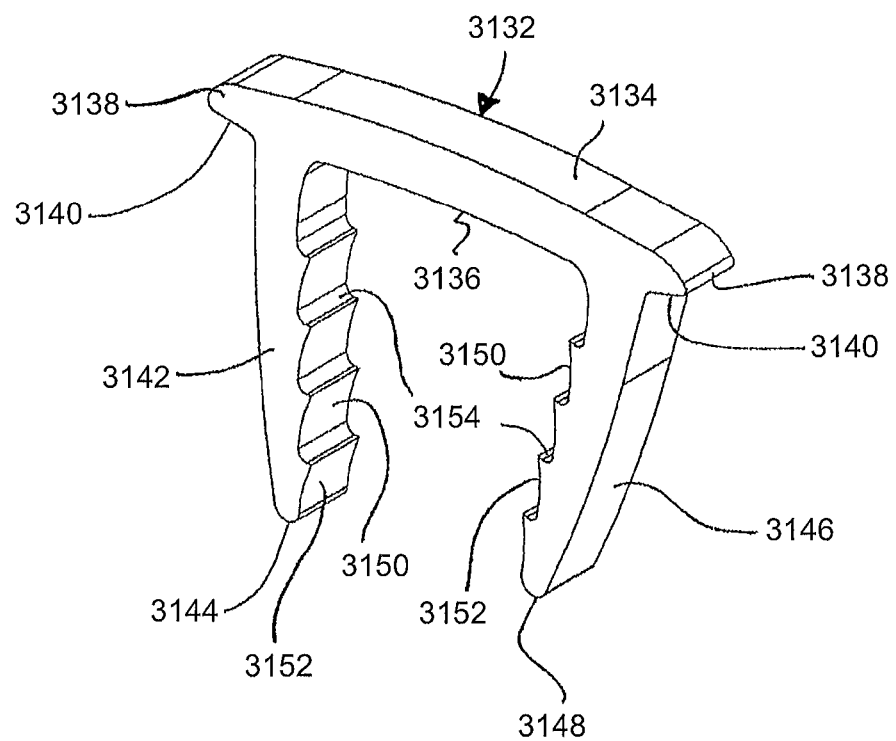
FIG. 10 is a perspective view of the staple of the staple insertion assembly of FIG. 1, in accordance with an aspect of the present invention.
Figure 11:
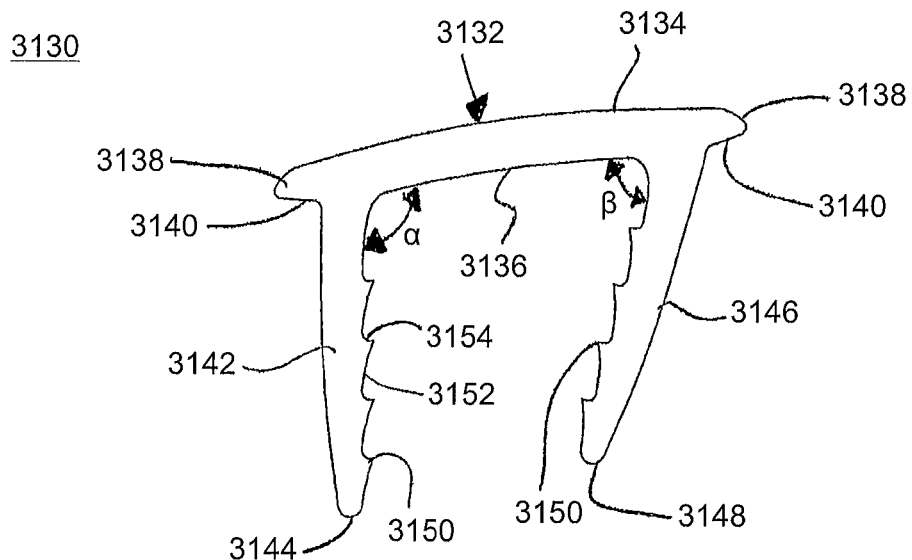
FIG. 11 is a front view of the staple of FIG. 10, in accordance with an aspect of the present invention.
Figure 12:
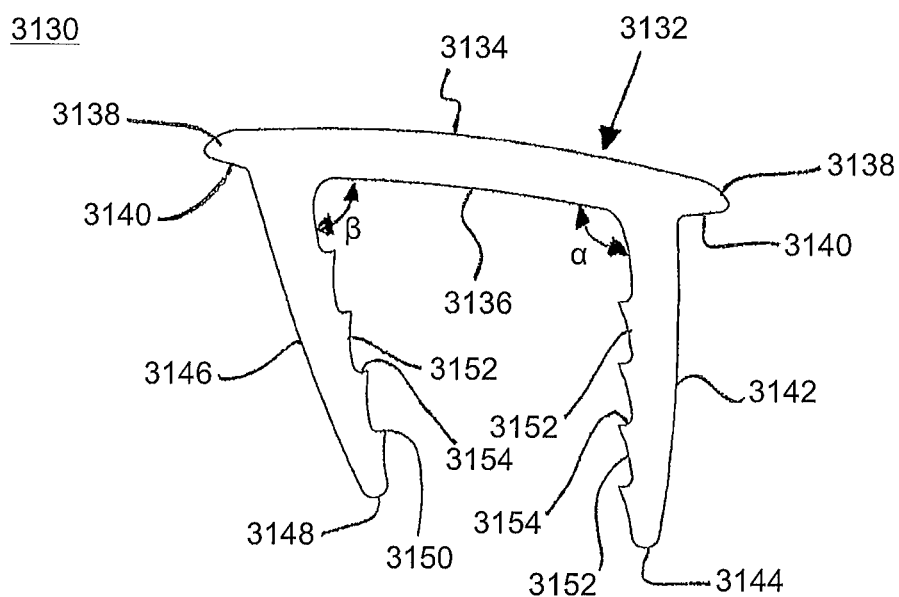
FIG. 12 is a rear view of the staple of FIG. 10, in accordance with an aspect of the present invention.
Figure 13:
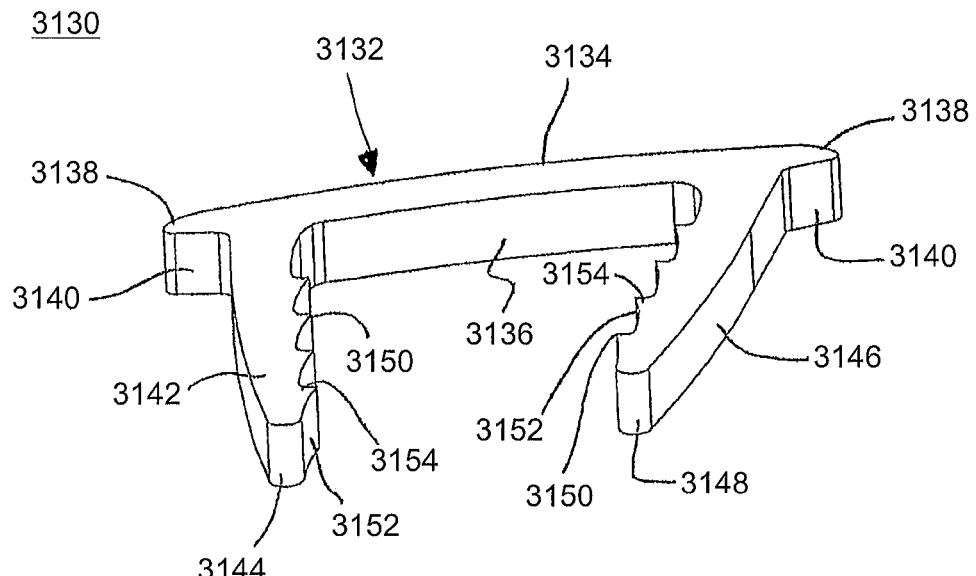
FIG. 13 is a first end view of the staple of FIG. 10, in accordance with an aspect of the present invention.
Figure 14:
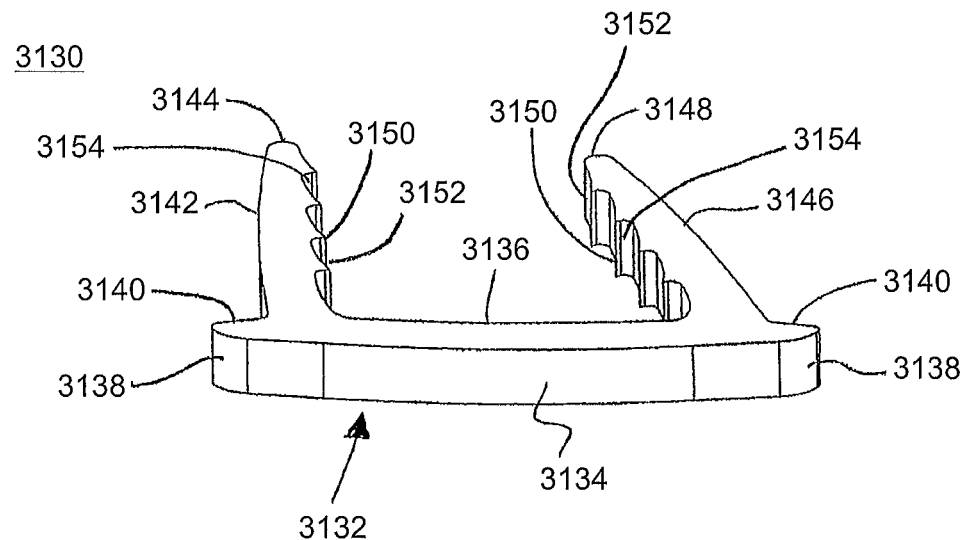
FIG. 14 is a second end view of the staple of FIG. 10, in accordance with an aspect of the present invention.

As best seen in FIGS. 1, 3, and 4, the second end 3104 of the holder 3100 is angled from a first side 3112 to a second side 3114. The second end 3104 also includes a receiving portion or recessed region 3116. The receiving portion 3116 extends, for example, through the entire width of the holder 3100 from the front side to the back side. The receiving portion 3116 is configured or sized and shaped to receive a staple 3130. The receiving portion 3116 includes contact portions or contact regions 3118 positioned on each side of the slot 3110. The contact portions 3118 extend from the opening of the slot 3110 toward the sides 3112, 3114. The receiving portion 3116 may also include recessed regions, gaps or reliefs 3120 and engagement members 3122. The recessed regions 3120 may be positioned between the contact portions 3118 and the engagement members 3122. The recessed regions 3120 may extend into the body 3100 past the contact portions 3118. Each recessed region 3120 and contact portion 3118 pair form a stepped region with the recessed region 3120 offset or stepped down from the contact portion 3118. The engagement members 3122 are, for example, projections extending from the sides 3112, 3114 toward the slot 3110. The engagement members 3122 form the ends of the recessed regions 3120 and are configured or sized and shaped to receive the ends of a staple 3130. The engagement members 3122 may be, for example, curved to form hook members to receive the staple 3130.

Figure 39:
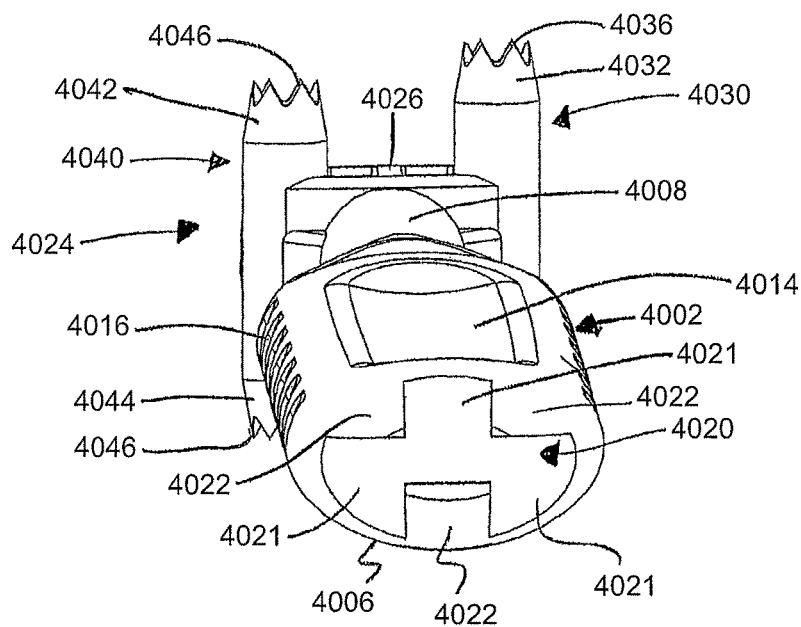
FIG. 39 is an end perspective view of the staple insertion instrument of FIG. 30, in accordance with an aspect of the present invention.
Figure 40:
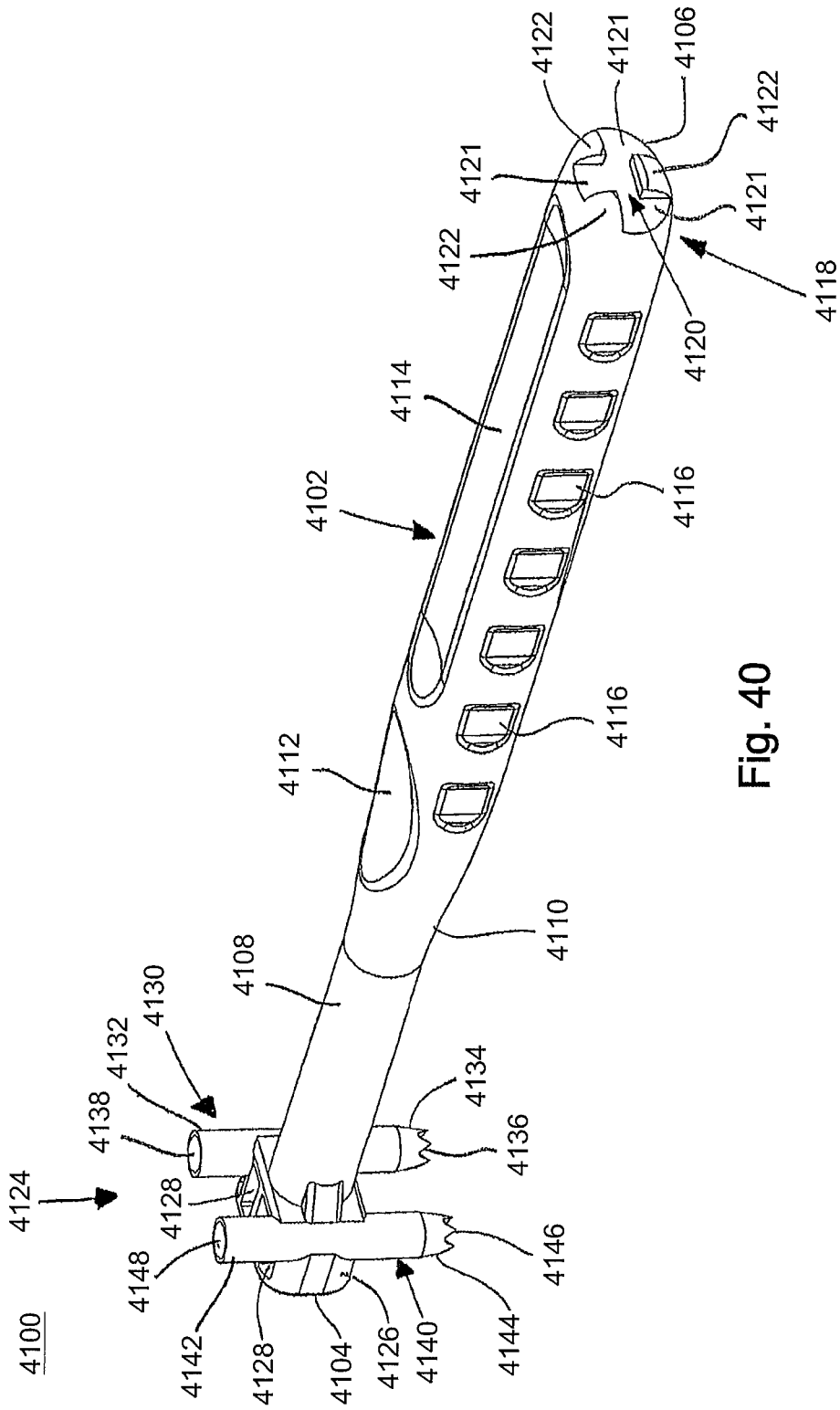
FIG. 40 is a first perspective view of another staple insertion instrument, in accordance with an aspect of the present invention.
Figure 41:
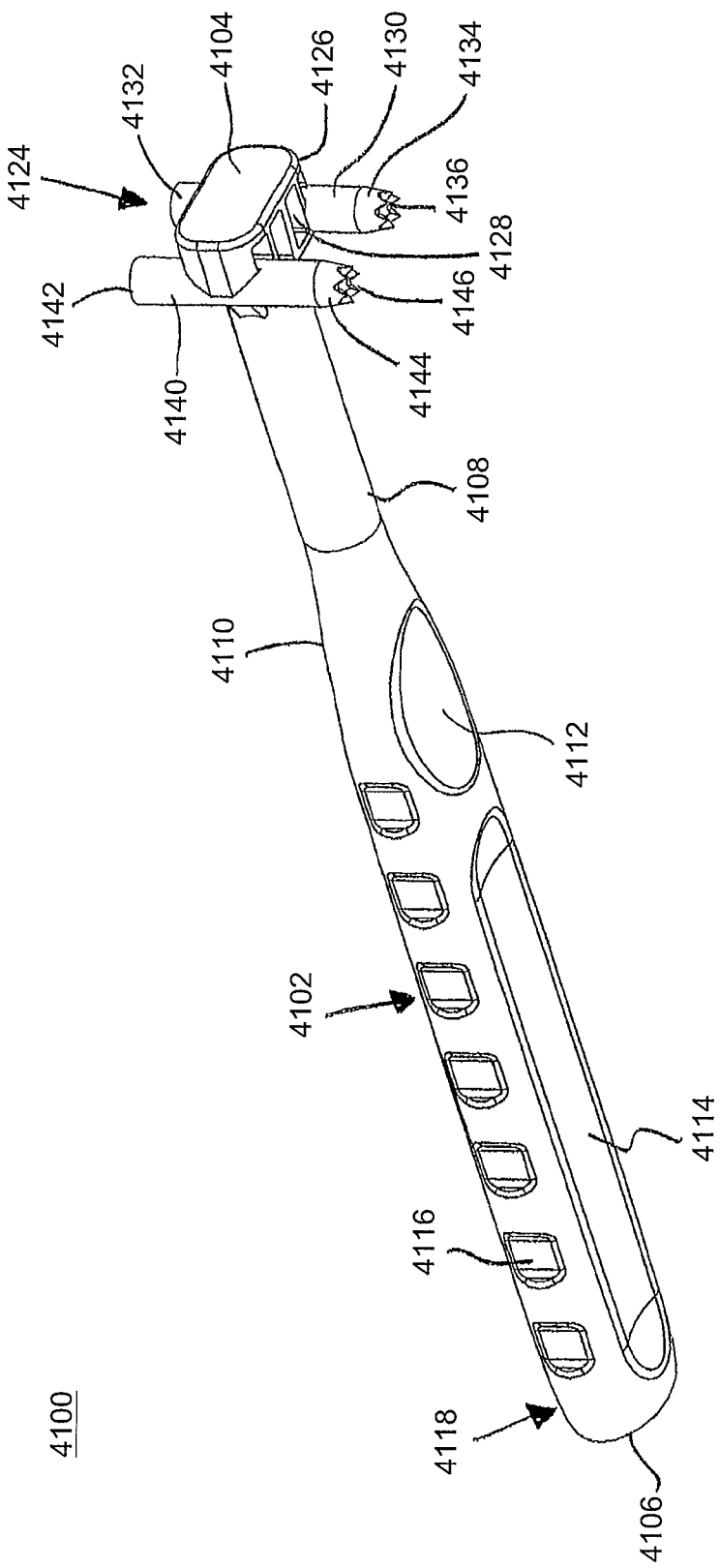
FIG. 41 is a second perspective view of the staple insertion instrument of FIG. 40, in accordance with an aspect of the present invention.
Figure 42:
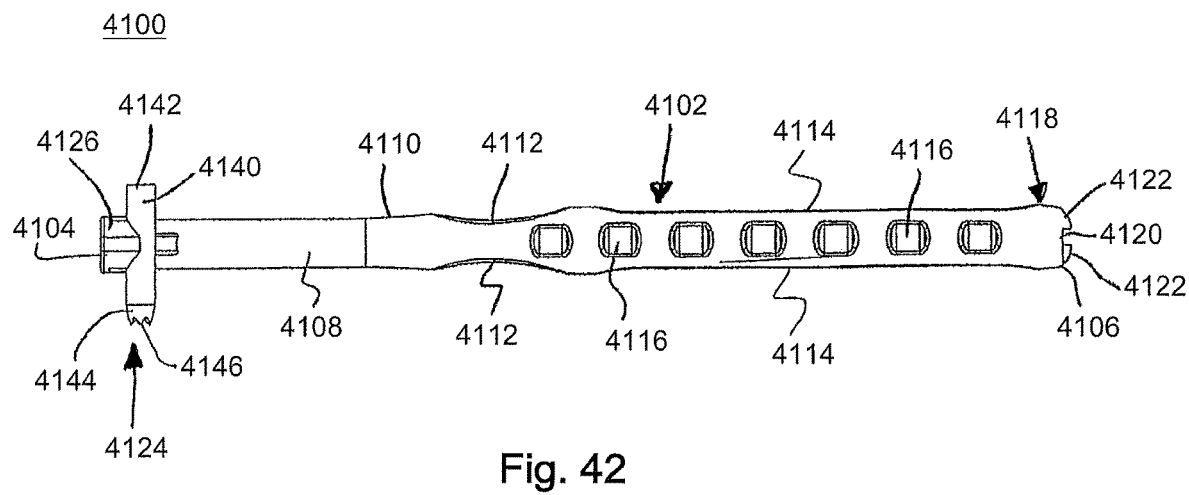
FIG. 42 is a first side view of the staple insertion instrument of FIG. 40, in accordance with an aspect of the present invention.
Figure 43:
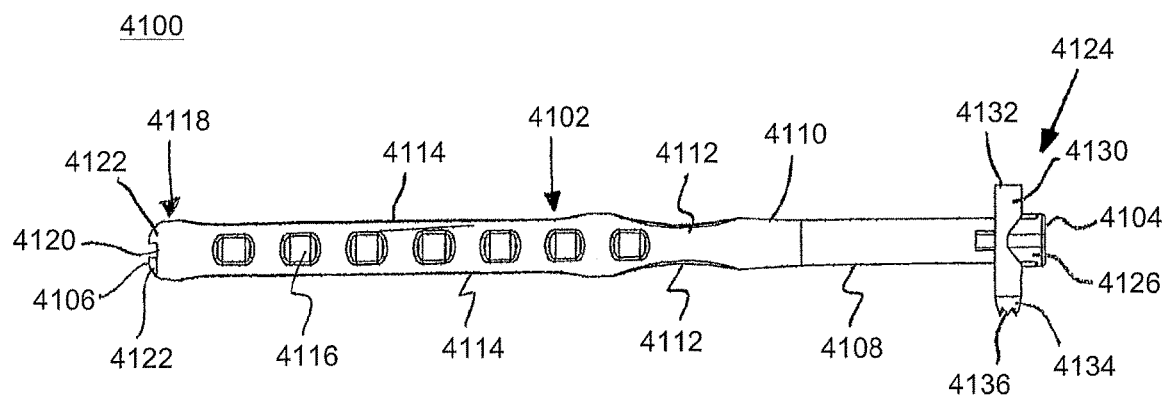
FIG. 43 is a second side view of the staple insertion instrument of FIG. 40, in accordance with an aspect of the present invention.
Figure 44:
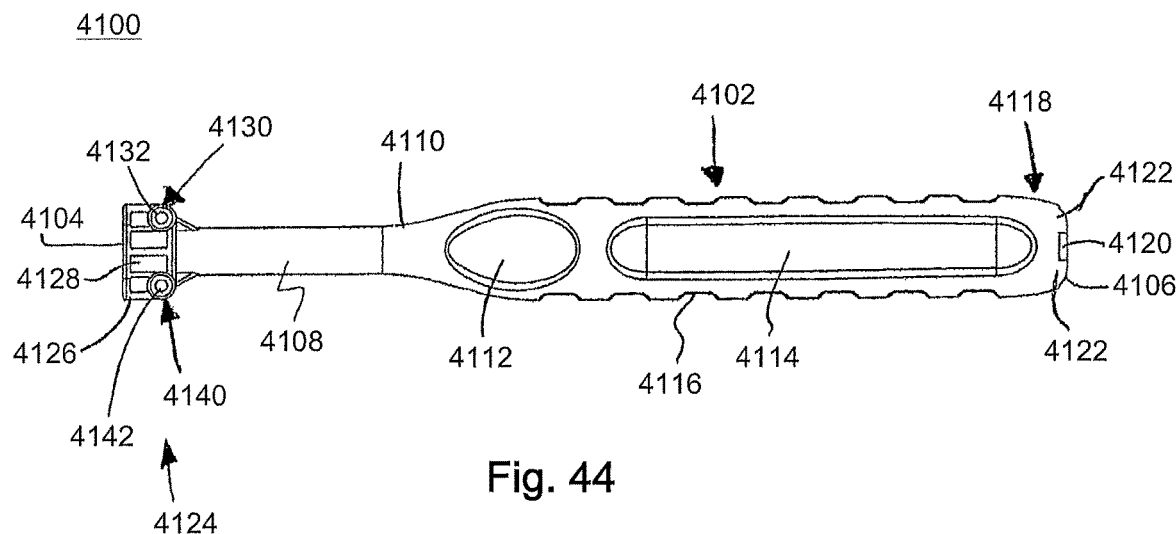
FIG. 44 is a top view of the staple insertion instrument of FIG. 40, in accordance with an aspect of the present invention.
Figure 45:
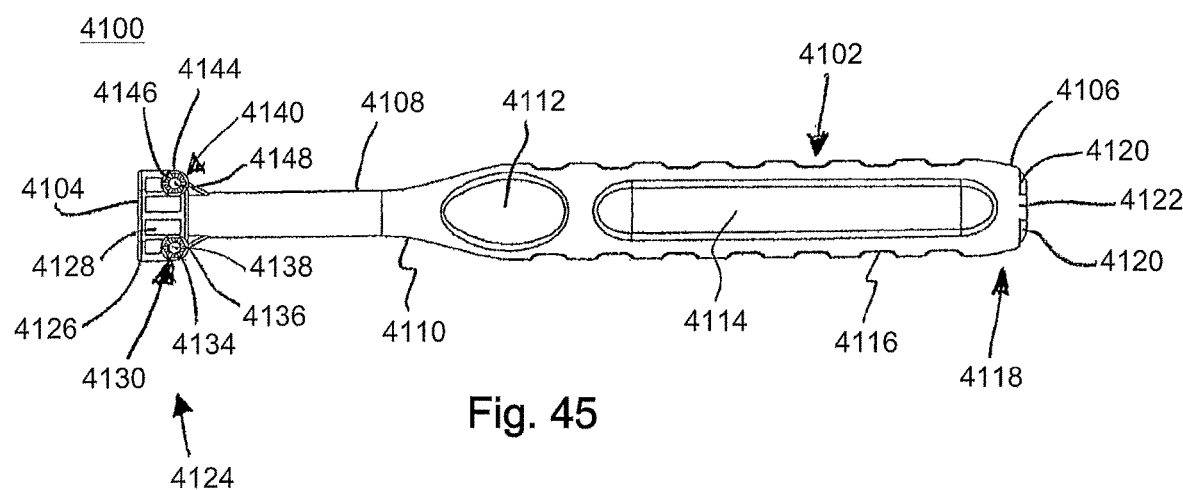
FIG. 45 is a bottom view of the staple insertion instrument of FIG. 40, in accordance with an aspect of the present invention.

The staple 3130 may include a base or bridge portion 3132 and two legs 3142, 3146, as shown in FIGS. 10-14. The bridge portion 3132 may include a top surface 3134 and a bottom surface 3136 opposite the top surface 3134. The bridge portion 3132 may also include extension portions, ears, or tabs 3138 extending away from each end. The extension portions 3138 may each include an engagement surface or engagement portion 3140. The engagement portions 3140 may be configured or sized and shaped to engage the engagement members 3122 of the holder 3100. The extension portions 3138 may be, for example, curved or rounded to match the shape of the ends of the receiving portion 3116 of the holder 3100. As shown in FIGS. 39 and 40, the bridge portion 3132 may be, for example, non-linear or angled as it extends between the extension portions 3138.

With continued reference to FIGS. 10-14, the legs 3142, 3146 may extend away from the bottom surface 3136 of the staple 3130. The first leg 3142 may extend from the bottom surface 3136 of the staple 3130 to a first tip 3144 and the second leg 3146 may extend from the bottom surface 3136 of the staple 3130 to a second tip 3148. The legs 3142, 3146 may each be, for example, tapered as they extend from the bottom surface 3136 of the staple 3130 to the tips 3144, 3148. Each leg 3142, 3146 may be positioned near an end of the bridge portion 3132 adjacent to the engagement surfaces or portions 3140. The first leg 3142 may, for example, extend from the bridge portion 3132 at a first angle $\alpha$ and the second leg 3146 may, for example, extend from the bridge portion 3132 at a second angle $\beta$. The two legs 3142, 3146 may form a third angle $\theta$ (not shown) at a point where the longitudinal axes of the legs 3142, 3146 would intersect. The first angle $\alpha$ may be, for example, approximately 80°-90°, and more preferably approximately 90°. The second angle $\beta$ may be, for example, approximately 30°-75°, and more preferably approximately 60°. The third angle $\theta$ (not shown) may be, for example, approximately 15°-70°, and more preferably approximately 30°. The first angle $\alpha$ may be, for example, greater than the second angle $\beta$. The second leg 3146 may be, for example, angled or tapered more than the first leg 3142 as the legs 3142, 3146 extend from the bridge portion 3132. The legs 3142, 3146 may each include at least one barb 3150 positioned on an interior surface of the legs 3142, 3146, as shown in FIGS. 10-14. Each barb 3150 may include, for example, a slightly inclined wall 3152 and a perpendicularly protruding wall 3154 forming a sharp edge to engage a patient's bones or bone fragments.

Figure 2:
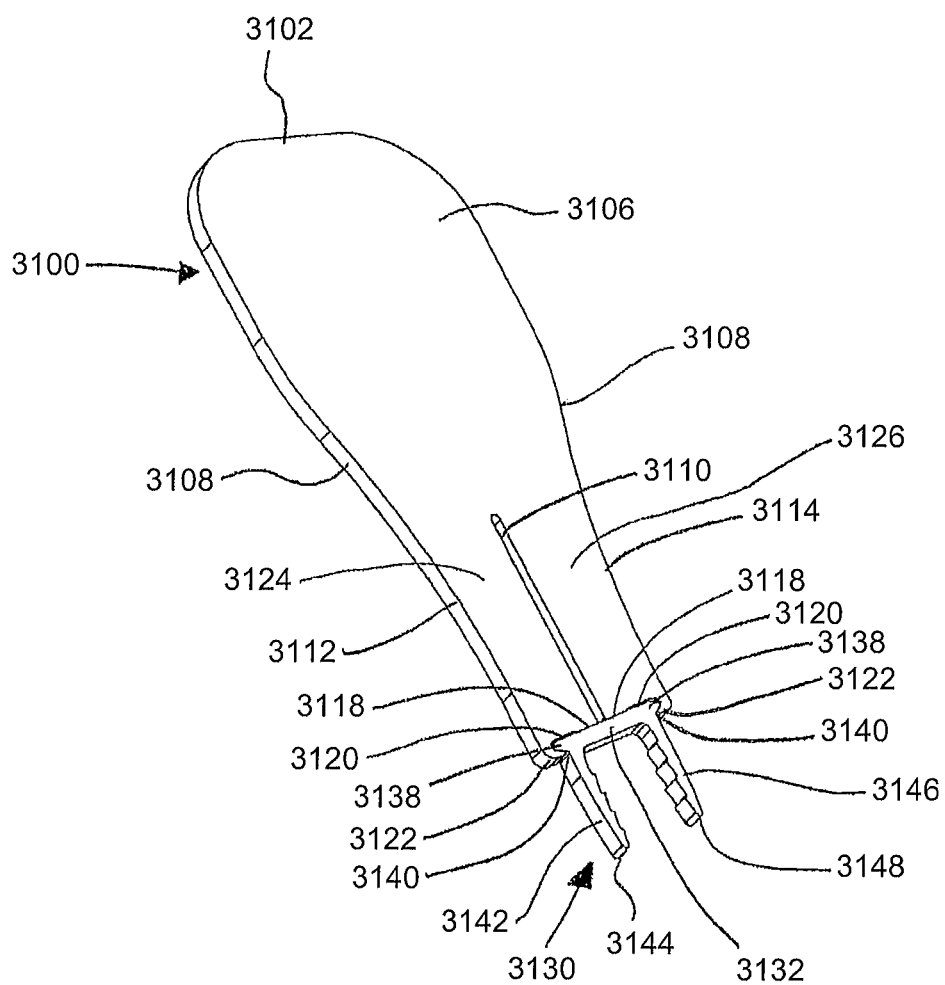
FIG. 2 is a perspective view of the staple insertion assembly of FIG. 1, in accordance with an aspect of the present invention.

As shown in FIGS. 1 and 2, the receiving portion 3116 of the holder 3100 receives the staple 3130. For example, the extension portions 3138 are positioned within the receiving portion 3116, the engagement surfaces 3140 contact the engagement members 3122, and the staple contact portions 3118 contact the top surface 3134 of the staple 3130 to position the staple 3130 in an open position for insertion into a bone. In the open position, the legs 3142, 3146 are moved laterally away from each other to an expanded position, where the legs 3142, 3146 are positioned generally parallel to each other. The contact portions 3118 make contact with the top surface 3134 of the staple 3130 near a middle portion of the staple 3130 and the engagement members 3122 make contact with the ends of the staple 3130 positioning the staple 3130 to form an opening between the top surface 3134 of the staple 3130 and the recessed regions 3120 of the holder 3100, as shown in FIGS. 1 and 2. Thus, the staple insertion assembly 3000 has, for example, four points of contact between the staple 3130 and the holder 3100.

Figure 15:
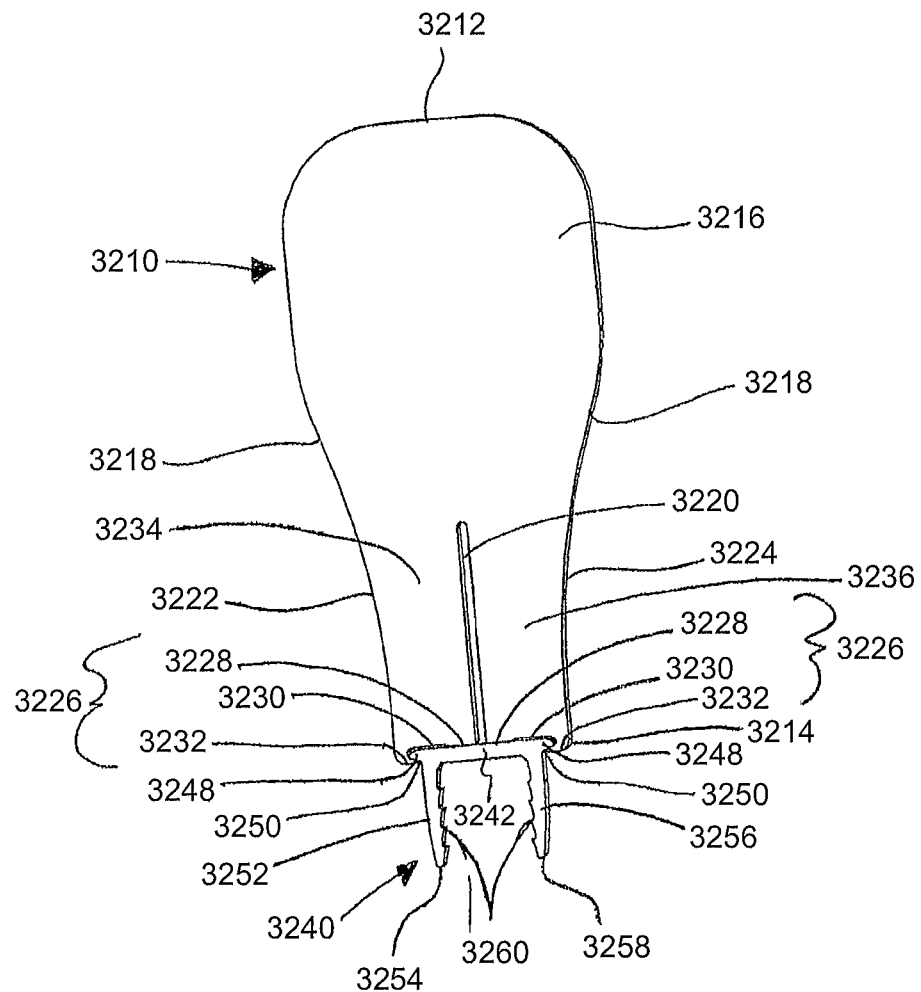
FIG. 15 is a front view of another embodiment of a staple insertion assembly, in accordance with an aspect of the present invention.
Figure 16:
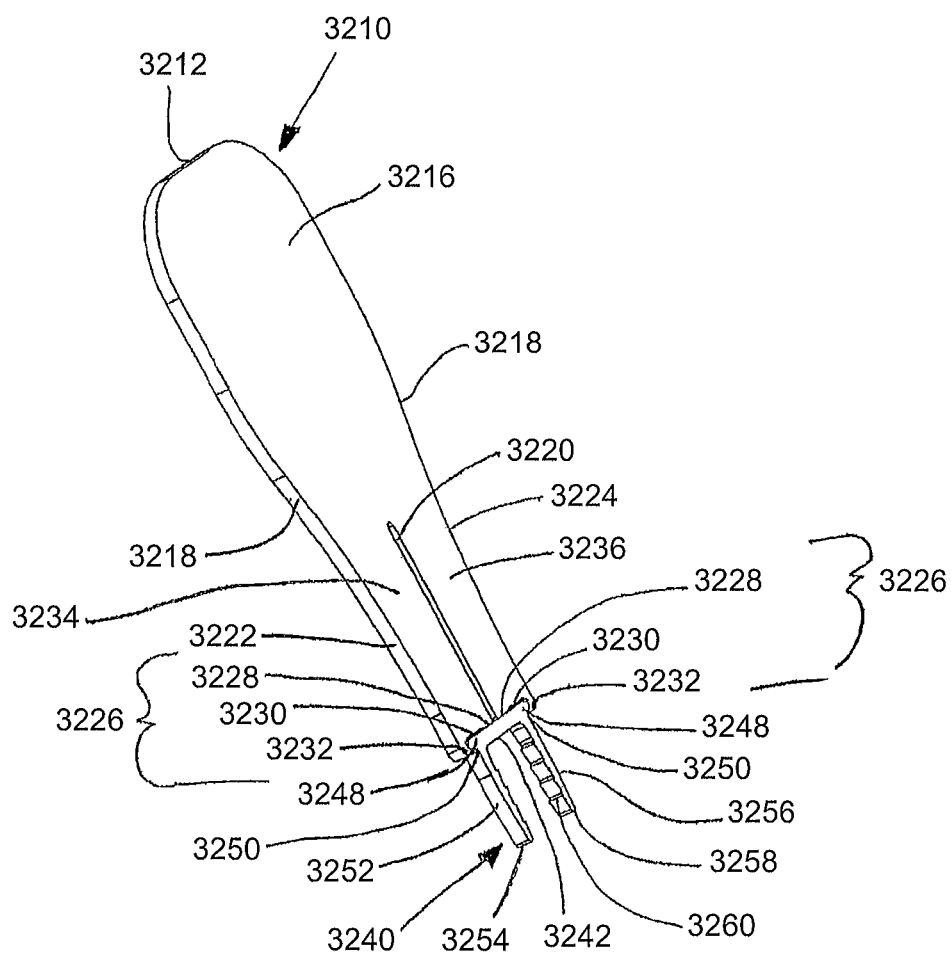
FIG. 16 is a perspective view of the staple insertion assembly of FIG. 15, in accordance with an aspect of the present invention.

Referring now to FIGS. 15-26, a straight staple insertion assembly 3200 is shown in FIGS. 15 and 16. The straight staple insertion assembly 3200 includes a staple holder 3210 and a staple 3240. The staple 3240 is received within a second end 3214 of the staple holder 3210 for insertion into a bone. The holder 3210 may be used for, for example, final placement of the staple 3240, pre-compression of the surgical site, for compression and in-vivo fixation when the stored energy within the staple 3240 is released.

The staple holder or body 3210, as shown in FIGS. 17-22, includes a first end 3212 and a second end 3214. The first end 3212 includes a gripping portion or handle portion 3216 for grasping during insertion of the staple 3240 into a bone. The gripping portion 3216 may extend from the first end 3212 to approximately a mid-point of the holder 3210 where the holder 3210 has curved or tapered sides 3218. The holder 3210 tapers, for example, from the curved sides 3218 toward the second end 3214. The holder 3210 may also optionally include, for example, a channel or slot 3220 extending from the second end 3214 into the body 3210 toward the first end 3212. The length of the slot 3220 may vary, for example, the slot 3220 may extend a given percentage of the length of the holder 3210. In an embodiment, the length of the slot 3220 may be, for example, approximately 20% to 55% of the height of the holder 3210, more specifically, approximately 34.5% of the height of the holder 3210. As shown in the depicted embodiment, the slot 3220 may be positioned, for example, at a center of the second end 3214. It is also contemplated that the slot 3220 may be offset from the center of the second end 3214. Further, it is also contemplated that the slot 3220 may be, for example, more than one slot 3220, specifically, if the holder 3210 receives, for example, a stepped staple (not shown). The slot 3220 may separate a portion of the holder 3210 to define a first member 3234 and a second member 3236 extending from the second end 3214 of the holder 3210. The first member 3234 may be, for example, a mirror image of the second member 3236.

Figure 17:
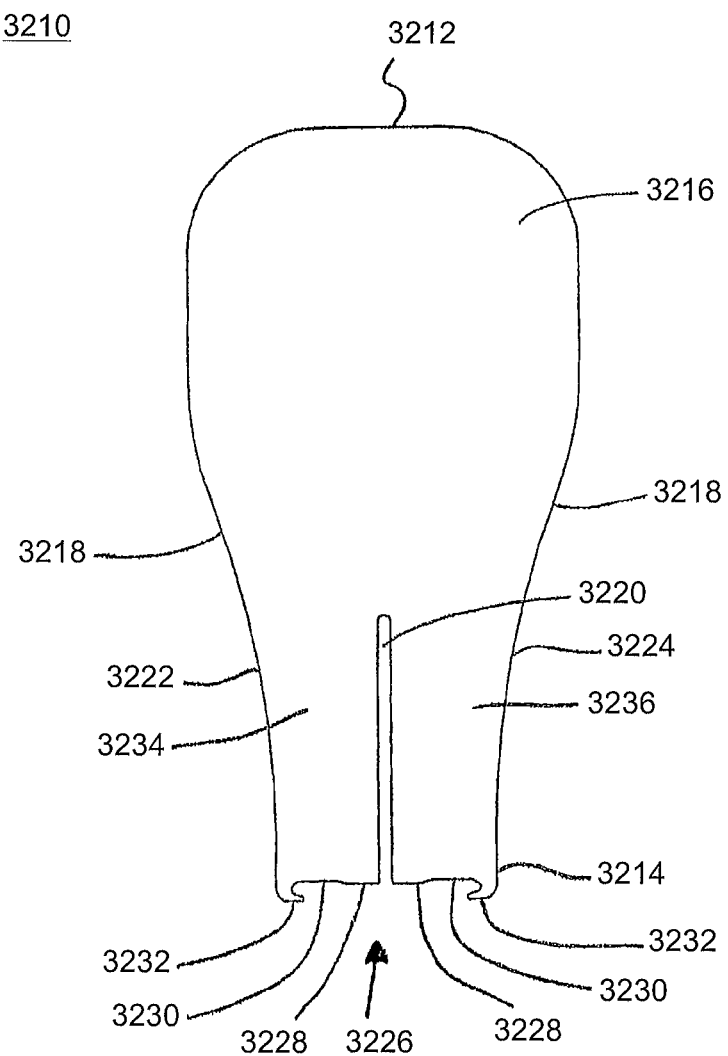
FIG. 17 is a front view of the staple holder of the staple insertion assembly of FIG. 15, in accordance with an aspect of the present invention.
Figure 18:
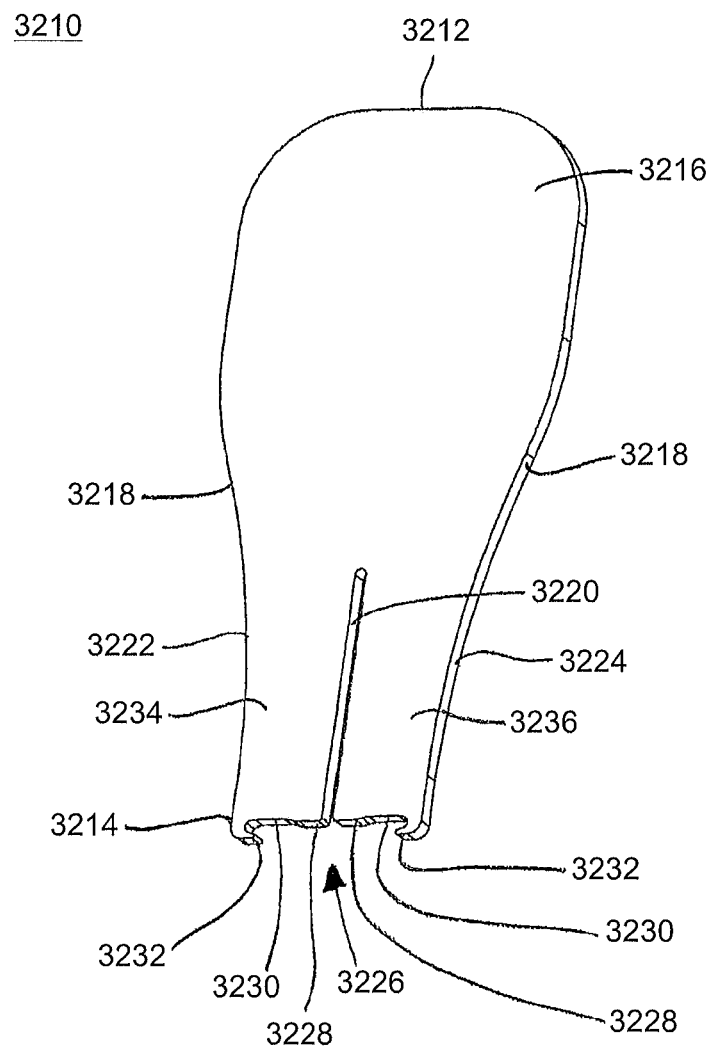
FIG. 18 is a front perspective view of the staple holder of FIG. 15, in accordance with an aspect of the present invention.
Figure 21:
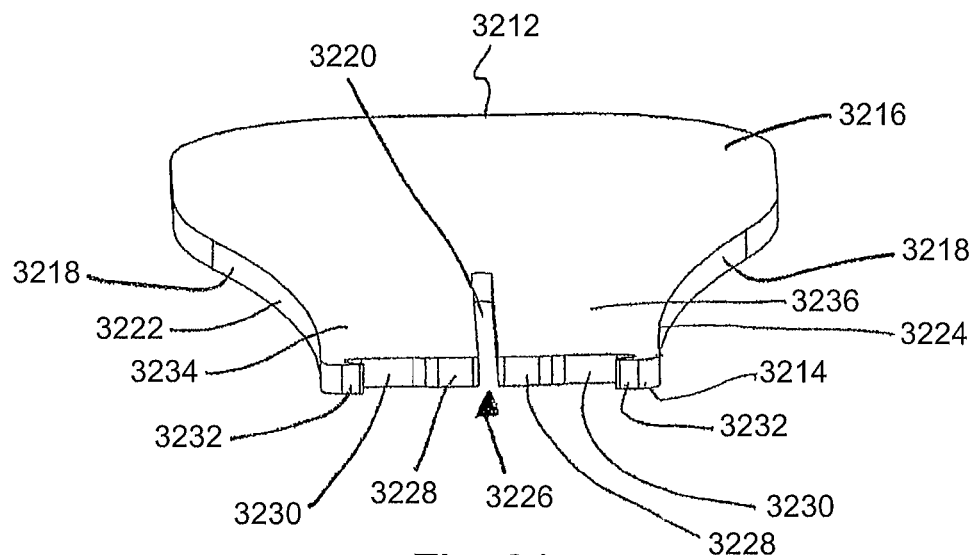
FIG. 21 is a first end perspective view of the staple holder of FIG. 17, in accordance with an aspect of the present invention.
Figure 22:
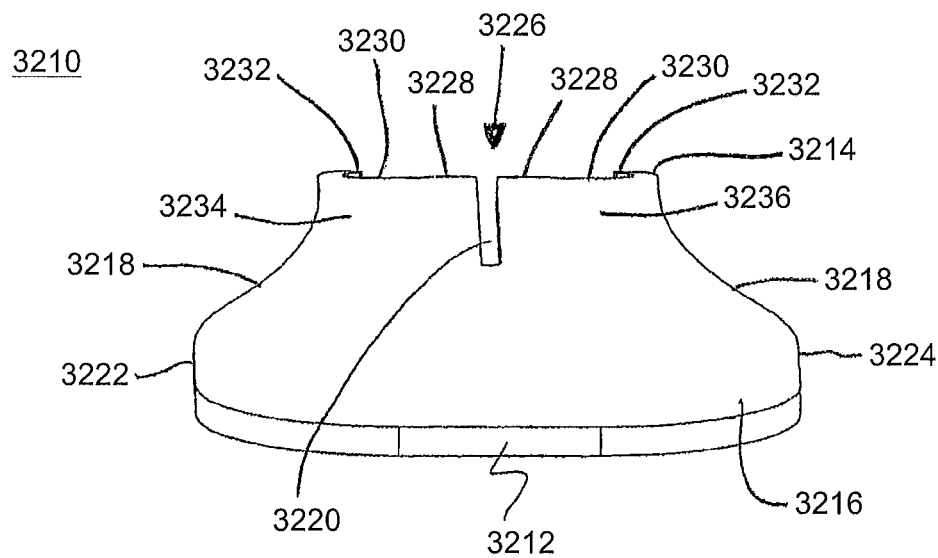
FIG. 22 is a second end perspective view of the staple holder of FIG. 17, in accordance with an aspect of the present invention.
Figure 23:
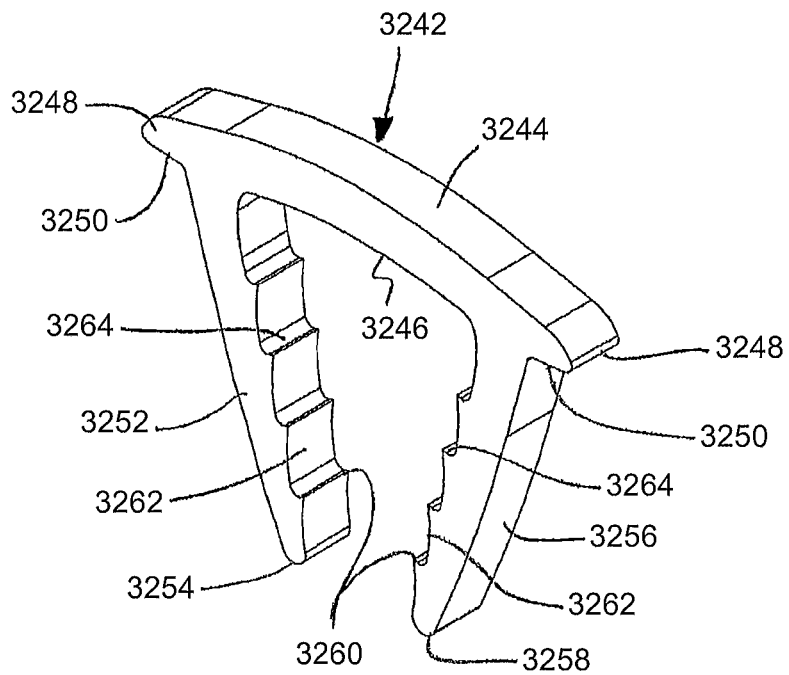
FIG. 23 is a front perspective view of the staple of the staple insertion assembly of FIG. 15, in accordance with an aspect of the present invention.

As best seen in FIGS. 15, 17, and 18, the second end 3214 of the holder 3210 is straight from a first side 3222 to a second side 3224. The second end 3214 also includes a receiving portion or recessed region 3226. The receiving portion 3226 extends, for example, through the entire width of the holder 3210 from the front side to the back side. The receiving portion 3226 is configured or sized and shaped to receive a staple 3240. The receiving portion 3226 includes contact portions or contact regions 3228 positioned on each side of the slot 3220. The contact portions 3228 extend from the opening of the slot 3220 toward the sides 3222, 3224.

The receiving portion 3226 may also include recessed regions, gaps or reliefs 3230 and engagement members 3232. The recessed regions 3230 may be positioned between the contact portions 3228 and the engagement members 3232. The recessed regions 3230 may extend into the body 3210 past the contact portions 3228. Each pair of recessed region 3230 and contact portion 3228 form a stepped region with the recessed region 3230 offset or stepped down from the contact portion 3228. The engagement members 3232 are, for example, projections extending from the sides 3222, 3224 toward the slot 3220. The engagement members 3232 form the ends of the recessed regions 3230 and are configured or sized and shaped to receive the ends of a staple 3240. The engagement members 3232 may be, for example, hook-like or curved to couple the ends of the staple 3240 to the holder 3210.

Figure 24:
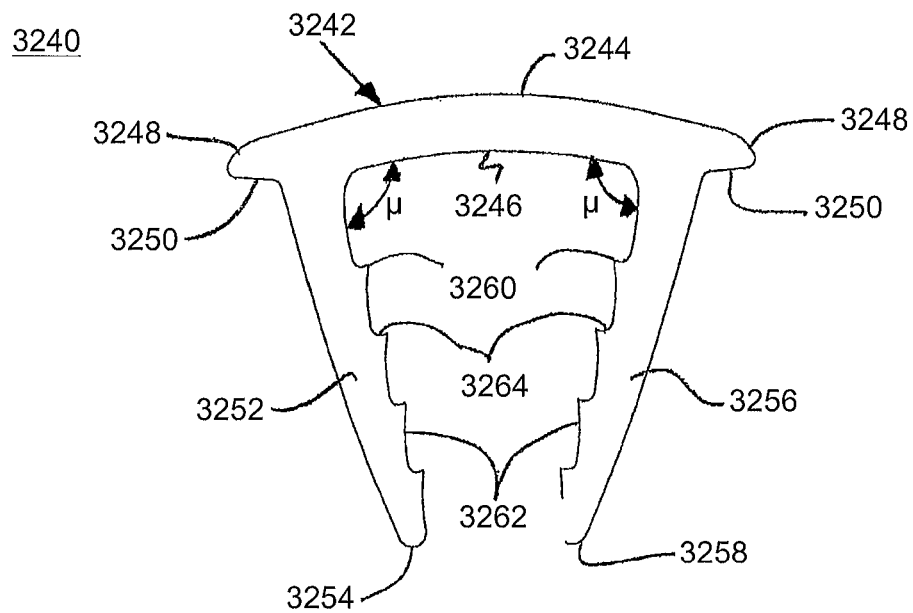
FIG. 24 is a rear view of the staple of FIG. 23, in accordance with an aspect of the present invention.
Figure 25:
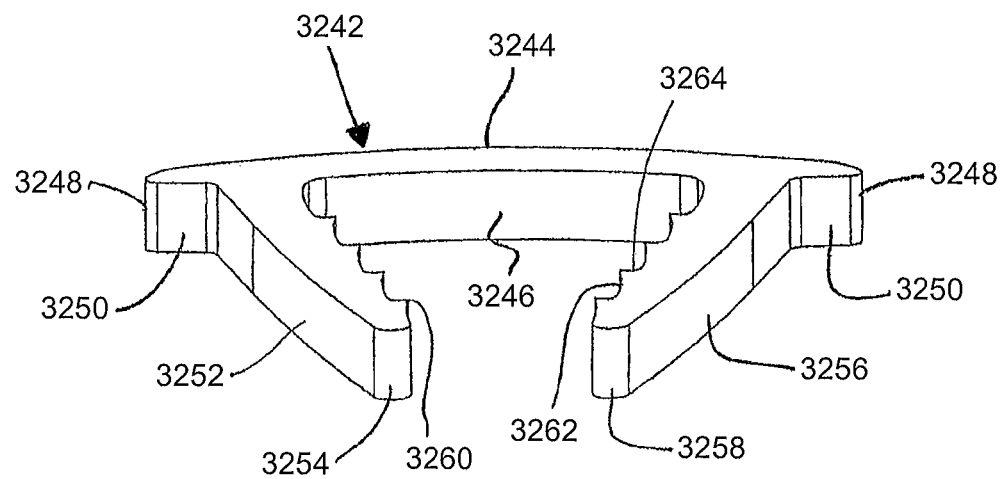
FIG. 25 is a first end view of the staple of FIG. 23, in accordance with an aspect of the present invention.
Figure 26:
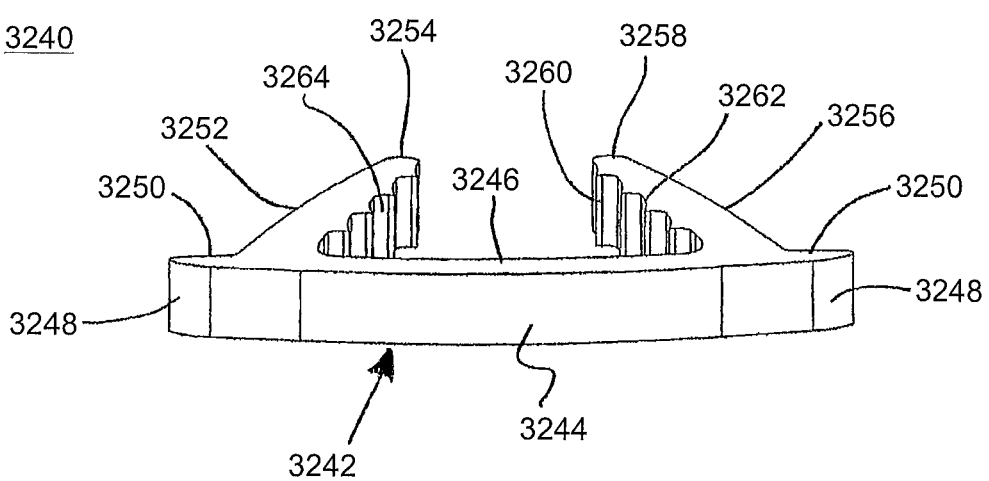
FIG. 26 is a second end view of the staple of FIG. 23, in accordance with an aspect of the present invention.

The staple 3240 may include a base or bridge portion 3242 and two legs 3252, 3256, as shown in FIGS. 23-26. The bridge portion 3242 may include a top surface 3244 and a bottom surface 3246 opposite the top surface 3244. The bridge portion 3242 may also include extension portions, ears, or tabs 3248 extending away from each end (i.e., laterally outside or away from the legs 3252, 3256). The extension portions 3248 may each include an engagement surface or engagement portion 3250. The engagement portions 3250 may be configured or sized and shaped to engage the engagement members 3232 of the holder 3210. The extension portions 3248 may be, for example, curved or rounded to match the shape of the ends of the receiving portion 3226 of the holder 3210. As shown in FIG. 24, the bridge portion 3242 may be, for example, generally straight with a curved top surface 3244 as it extends between the extension portions 3248.

With continued reference to FIGS. 23-26, the legs 3252, 3256 may extend away from the bottom surface 3246 of the staple 3240. The first leg 3252 may extend from the bottom surface 3246 of the staple 3240 to a first tip 3254 and the second leg 3256 may extend from the bottom surface 3246 of the staple 3240 to a second tip 3258. The legs 3252, 3256 may each be, for example, tapered as they extend from the bottom surface 3246 of the staple 3240 to the tips 3254, 3258. Each leg 3252, 3256 may be positioned near an end of the bridge portion 3242 adjacent to the engagement surfaces or portions 3250. The first and second legs 3252, 3256 may, for example, each extend from the bridge portion 3242 at an angle $\mu$. The two legs 3252, 3256 may form an angle $\theta$ (not shown) at a point where the longitudinal axes of the legs 3252, 3256 intersect. The angles $\mu$ may be, for example, approximately 48.75°-82.5°, and more preferably approximately 60°. The angle $\theta$ (not shown) may be, for example, approximately 15°-48°, and more preferably approximately 30°. The legs 3252, 3256 may also each include at least one barb 3260 positioned on an interior surface of the legs 3252, 3256, as shown in FIGS. 23-26. Each barb 3260 may include, for example, a slightly inclined wall 3262 and a perpendicularly protruding wall 3264 forming a sharp edge to engage a surface of the bones or bone fragments.

As shown in FIGS. 15 and 16, the receiving portion 3226 of the holder 3210 receives the staple 3240. For example, the extension portions 3248 are positioned within the receiving portion 3226, the engagement surfaces 3250 contact the engagement members 3232, and the staple contact portions 3228 contact the top surface 3244 of the staple 3240 to position the staple 3240 in an open position for insertion into a bone. In the open position, the legs 3252, 3256 are moved laterally away from each other to an expanded position, where the legs 3252, 3256 are positioned generally parallel to each other. The contact portions 3228 make contact with the top surface 3244 of the staple 3240 near a middle portion of the staple 3240 and the engagement members 3232 make contact with the ends of the staple 3240 positioning the staple 3240 to form an opening between the top surface 3244 of the staple 3240 and the recessed regions 3230 of the holder 3210, as shown in FIGS. 15 and 16. Thus, the staple insertion assembly 3200 has, for example, four points of contact between the staple 3240 and the holder 3210.

Figure 27:
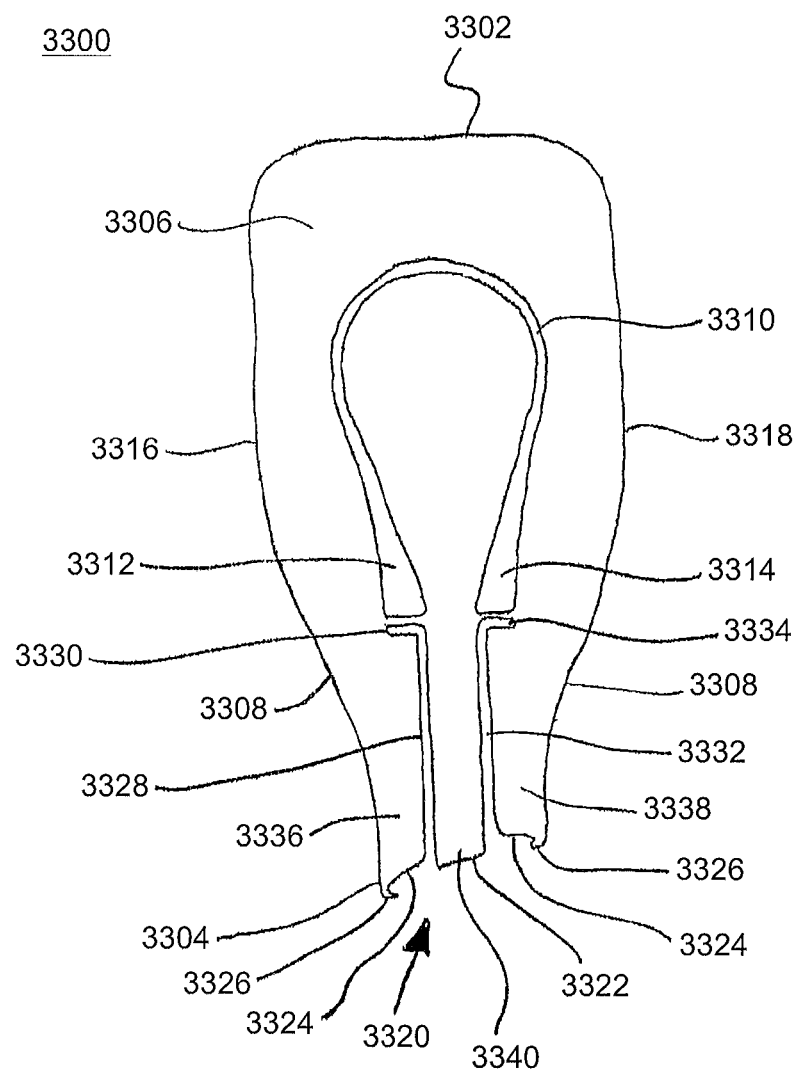
FIG. 27 is a front view of another embodiment of a staple holder, in accordance with an aspect of the present invention.

Referring now to FIG. 27, another staple holder 3300 for an angled staple insertion assembly is shown. The angled staple holder 3300 receives a staple 3130, as described in greater detail above and which will not be described again here for brevity sake. The staple 3130 is received within a second end 3304 of the staple holder 3300 for insertion into a patient. The holder 3300 may be used for final placement of the staple 3130, pre-compression of the surgical site if desired, release of energy within the staple 3130 for compression and in-vivo fixation.

The staple holder or body 3300, as shown in FIG. 27, includes a first end 3302 and a second end 3304. The first end 3302 includes a gripping portion or handle portion 3306 for grasping during insertion of the staple 3130 into a patient. The gripping portion 3306 may extend from the first end 3302 toward the second end 3304 and include curved or tapered sides 3308 positioned between the first end 3302 and second end 3304. The holder 3300 tapers from the curved sides 3308 toward the second end 3304. The holder 3300 may also optionally include, for example, a curved channel 3310 positioned within the gripping portion 3306. The curved channel 3310 may, for example, form a loop or open teardrop shape. The curved channel 3310 may include a first channel end 3312 and a second channel end 3314. The channel ends 3312, 3314 may extend out from the channel 3310 and expand as they extend toward the second end 3304. The open channel ends 3312, 3314 may have, for example, a generally triangular shape, although other shapes are also contemplated. The length and curvature of the channel 3310 may vary, for example, the channel 3310 may extend a given percentage of the length of the holder 3300. The channel 3310 may be positioned, for example, at a center of the holder 3300. For example, the channel 3310 may be positioned between the first side 3316 and the second side 3318.

With continued reference to FIG. 27, the holder 3300 may also include a first slot 3328 and a second slot 3332. The slots 3328, 3332 may be positioned, for example, to separate the second end 3304 of the holder 3300 into, for example, three portions, which may be three equal portions or three unequal portions. For example, the first slot 3328 may form a first member 3336 positioned on the first side 3316 of the holder 3300, the second slot 3332 may form a second member 3338 positioned on the second side 3318 of the holder 3300, and a third member 3340 may be formed between the first slot 3328 and the second slot 3332. The first slot 3328 may include a first foot portion 3330 at the top of the slot 3328. The foot portion 3330 may extend from the slot 3328 towards the first side 3316 of the holder 3300. The first foot portion 3330 may also be positioned, for example, under at least a portion of the first channel end 3312 of the curved channel 3310. In an embodiment, the first foot portion 3330 may be positioned, for example, directly under the first channel end 3312 of the curved channel 3310. The second slot 3332 may include a second foot portion 3334 at the top of the slot 3332. The second foot portion 3334 may extend from the slot 3332 towards the second side 3318 of the holder 3300. The second foot portion 3334 may also be positioned, for example, under at least a portion of the second channel end 3314 of the curved channel 3310. In an embodiment, the second foot portion 3334 may be positioned, for example, directly under the second channel end 3314 of the curved channel 3310.

As best seen in FIG. 27, the second end 3304 of the holder 3300 is angled from a first side 3316 to a second side 3318. The second end 3304 also includes a receiving portion or recessed region 3320. The receiving portion 3320 extends, for example, through the entire width of the holder 3300 from the front side to the back side. The receiving portion 3320 is configured or sized and shaped to receive a staple 3130. The receiving portion 3320 includes a contact portion or contact region 3322 positioned on a bottom of the third member 3340. The receiving portion 3320 may also include recessed regions, gaps or reliefs 3324 and engagement members 3326. The recessed regions 3324 may be positioned on the first member 3336 and second member 3338. The recessed regions 3324 may extend from the interior side of the first and second members 3336, 3338 to the engagement members 3326. The recessed regions 3324 may extend into the body 3300 past the contact portion 3322. The engagement members 3326 are, for example, projections extending from the sides 3316, 3318 toward the third member 3340. The engagement members 3326 form the ends of the recessed regions 3324 and are configured or sized and shaped to receive the ends of a staple 3130. The engagement portions 3140 of the staple 3130 may be configured or sized and shaped to engage the engagement members 3326 of the holder 3300. The extension portions 3138 of the staple 3130 may be, for example, curved or rounded to match the shape of the ends of the receiving portion 3320 of the holder 3300.

The receiving portion 3320 of the holder 3300 receives the staple 3130. For example, the extension portions 3138 are positioned within the receiving portion 3320, the engagement surfaces 3140 contact the engagement members 3326, and the staple contact portion 3322 contacts the top surface 3134 of the staple 3130 to position the staple 3130 in an open position for insertion into a bone. In the open position, the legs 3142, 3146 are moved laterally away from each other to an expanded position where the legs 3142, 3146 are positioned generally parallel to each other. The contact portion 3322 makes contact with the top surface 3134 of the staple 3130 near a middle portion of the staple 3130 and the engagement members 3326 make contact with the ends of the staple 3130, positioning the staple 3130 to form an opening between the top surface 3134 of the staple 3130 and the recessed regions 3324 of the holder 3300. Thus, the staple insertion assembly has, for example, four points of contact between the staple 3130 and the holder 3300.

Figure 28:
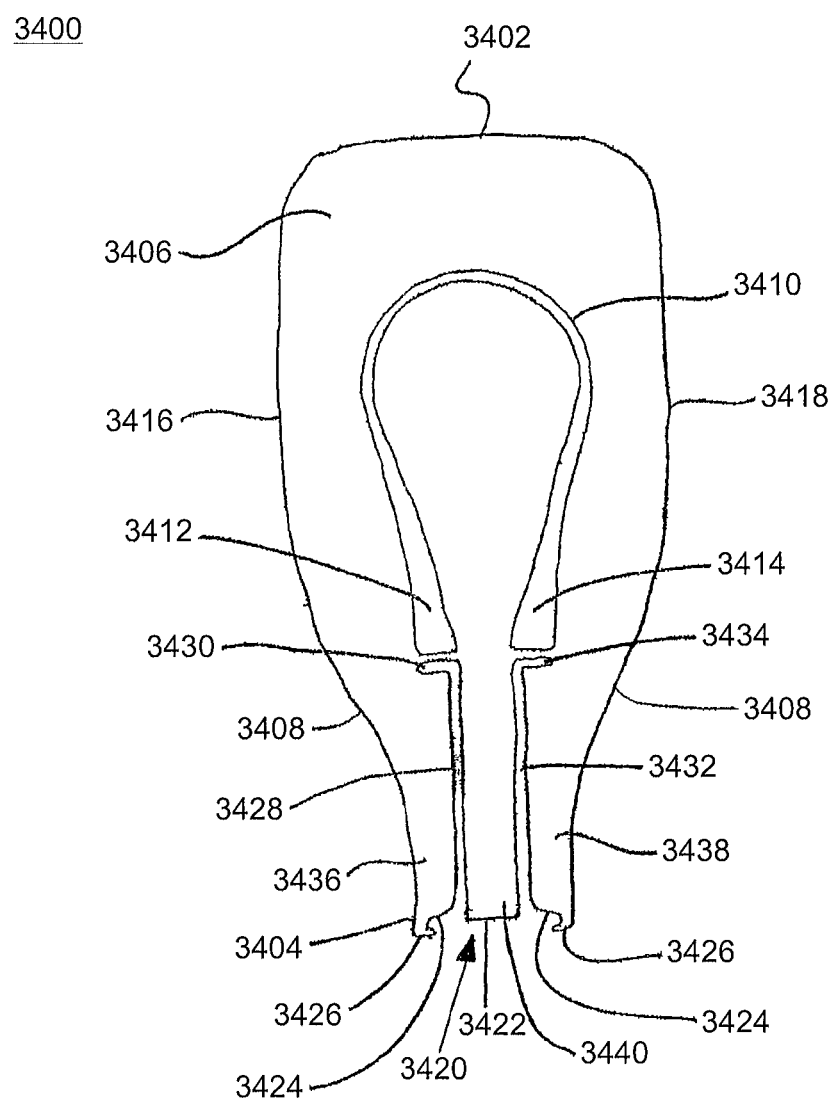
FIG. 28 is a front view of yet another embodiment of a staple holder, in accordance with an aspect of the present invention.

Referring now to FIG. 28, another staple holder 3400 for a straight staple insertion assembly is shown. The straight staple insertion assembly includes a staple holder 3400 and a staple 3240. The staple 3240 is received within a second end 3404 of the staple holder 3400 for insertion into a patient. The holder 3400 may be used for, for example, final placement of the staple 3240, pre-compression of the surgical site, for compression and in-vivo fixation when the energy within the staple 3240 is released.

The staple holder or body 3400, as shown in FIG. 28, includes a first end 3402 and a second end 3404. The first end 3402 includes a gripping portion or handle portion 3406 for grasping during insertion of the staple 3240 into a patient. The gripping portion 3406 may extend from the first end 3402 toward the second end 3404 and include curved or tapered sides 3408 positioned between the first end 3402 and second end 3404. The holder 3400 tapers from the curved sides 3408 toward the second end 3404. The holder 3400 may also optionally include, for example, a curved channel 3410 positioned within the gripping portion 3406. The curved channel 3410 may, for example, form a loop or open teardrop shape. The curved channel 3410 may include a first channel end 3412 and a second channel end 3414. The channel ends 3412, 3414 may extend out from the channel 3410 and expand as they extend toward the second end 3404. The channel ends 3412, 3414 may have, for example, a generally triangular shape, although other shapes are also contemplated. The length and curvature of the channel 3410 may vary, for example, the channel 3410 may extend a given percentage of the length of the holder 3400. The channel 3410 may be positioned, for example, at a center of the holder 3400. The channel 3410 may also be positioned between the first side 3416 and the second side 3418.

With continued reference to FIG. 28, the holder 3400 may also include a first slot 3428 and a second slot 3432. The slots 3428, 3432 may be positioned, for example, to separate the second end 3404 of the holder 3400 into, for example, three portions, which may be three equal portions or three unequal portions. For example, the first slot 3428 may form a first member 3436 positioned on the first side 3416 of the holder 3400, the second slot 3432 may form a second member 3438 positioned on the second side 3418 of the holder 3400, and a third member 3440 may be formed between the first slot 3428 and the second slot 3432. The first slot 3428 may include a first foot portion 3430 at the top of the slot 3428. The foot portion 3430 may extend from the first slot 3428 toward the first side 3416 of the holder 3400. The first foot portion 3430 may also be positioned, for example, under at least a portion of the first channel end 3412 of the curved channel 3410. In an embodiment, the first foot portion 3430 may be positioned, for example, directly under the first channel end 3412 of the curved channel 3410. The second slot 3432 may include a second foot portion 3434 at the top of the slot 3432. The foot portion 3434 may extend towards the second side 3418 of the holder 3400. The second foot portion 3434 may also be positioned, for example, under at least a portion of the second channel end 3414 of the curved channel 3410. In an embodiment, the second foot portion 3434 may be positioned, for example, directly under the second channel end 3414 of the curved channel 3410

As best seen in FIG. 28, the second end 3404 of the holder 3400 is straight from a first side 3416 to a second side 3418. The second end 3404 also includes a receiving portion or recessed region 3420. The receiving portion 3420 extends, for example, through the entire width of the holder 3400 from the front side to the back side. The receiving portion 3420 is configured or sized and shaped to receive a staple 3240. The receiving portion 3420 includes a contact portion or contact region 3422 positioned on a bottom of the third member 3440. The receiving portion 3420 may also include recessed regions, gaps or reliefs 3424 and engagement members 3426. The recessed regions 3424 may extend from the interior side of the first and second members 3436, 3438 to the engagement members 3426. The recessed regions 3424 may extend into the body 3400 past the contact portion 3422. The engagement members 3426 are, for example, projections extending from the sides 3416, 3418 toward the third member 3440. The engagement members 3426 form the ends of the recessed regions 3424 and are configured or sized and shaped to receive the ends of a staple 3240. The engagement portions 3250 may be configured or sized and shaped to engage the engagement members 3426 of the holder 3400. The extension portions 3248 may be, for example, curved or rounded to match the shape of the ends of the receiving portion 3420 of the holder 3400.

The receiving portion 3420 of the holder 3400 receives the staple 3240. For example, the extension portions 3248 are positioned within the receiving portion 3420, the engagement surfaces 3250 contact the engagement members 3426, and the staple contact portion 3422 contacts the top surface 3244 of the staple 3240 to position the staple 3240 in an open position for insertion into a bone. In the open position, the legs 3252, 3256 are moved laterally away from each other to an expanded position where the legs 3252, 3256 are positioned generally parallel to each other. The contact portion 3422 makes contact with the top surface 3244 of the staple 3240 near a middle portion of the staple 3240 and the engagement members 3426 make contact with the ends of the staple 3240, positioning the staple 3240 to form an opening between the top surface 3244 of the staple 3240 and the recessed regions 3424 of the holder 3400. Thus, the staple insertion assembly has four points of contact between the staple 3240 and the holder 3400.

Referring now to FIG. 29, another straight staple holder 3500 is shown. Another straight staple insertion assembly includes the staple holder 3500 and a staple 3240. The staple 3240 is received within a second end 3504 of the staple holder 3500 for insertion into a bone. The holder 3500 may be used for, for example, final placement of the staple 3240, pre-compression of the surgical site, for compression and in-vivo fixation when the energy within the staple 3240 is released.

The staple holder or body 3500, as shown in FIG. 29, includes a first end 3502 and a second end 3504. The first end 3502 includes a gripping portion or handle portion 3506 for grasping during insertion of the staple 3240 into a patient. The gripping portion 3506 may extend from the first end 3502 toward the second end 3504 of the holder 3500 and may include curved or tapered sides 3508. The holder 3500 tapers, for example, from the curved sides 3508 toward the first end 3502. The holder 3500 may also optionally include, for example, a channel or slot 3510 extending from the second end 3504 into the body 3500 toward the first end 3502. The length of the slot 3510 may vary, for example, the slot 3510 may extend a given percentage of the length of the holder 3500. The slot 3510 may be positioned, for example, at a center of the second end 3504. It is also contemplated that the slot 3510 may be offset from the center of the second end 3504. Further, it is also contemplated that the slot 3510 may be, for example, more than one slot 3510, specifically, if the holder 3500 receives, for example, a stepped staple (not shown). The slot 3510 may separate a portion of the holder 3500 to form a first member 3524 and a second member 3526 extending from the second end 3504 of the holder 3500. The first member 3524 may be, for example, a mirror image of the second member 3526.

As best seen in FIG. 29, the second end 3504 of the holder 3500 is straight from a first side 3512 to a second side 3514. The second end 3504 also includes a receiving portion or recessed region 3516. The receiving portion 3516 extends, for example, through the entire width of the holder 3500 from the front side to the back side. The receiving portion 3516 is configured or sized and shaped to receive a staple 3240. The receiving portion 3516 includes contact portions or contact regions 3518 positioned on each side of the slot 3510. The contact portions 3518 extend from the opening of the slot 3510 toward the sides 3512, 3514. The receiving portion 3516 may also include recessed regions, gaps or reliefs 3520 and engagement members 3522. The recessed regions 3520 may be positioned between the contact portions 3518 and the engagement members 3522. The recessed regions 3520 may extend into the body 3500 past the contact portions 3518. Each recessed region 3516 and contact portion 3518 pair form a stepped region with the recessed region 3520 offset or stepped down from the contact portion 3518. The engagement members 3522 are, for example, projections extending from the sides 3512, 3514 toward the slot 3510. The engagement members 3522 form the ends of the recessed regions 3520 and are configured or sized and shaped to receive the ends of a staple 3240. The engagement members 3522 may be, for example, curved to form hook-like members to receive the staple 3240.

The engagement portions 3250 of the staple 3240 may be configured or sized and shaped to engage the engagement members 3522 of the holder 3500. The extension portions 3248 may be, for example, curved or rounded to match the shape of the ends of the receiving portion 3516 of the holder 3500. The receiving portion 3516 of the holder 3500 receives the staple 3240. For example, the extension portions 3248 are positioned within the receiving portion 3516, the engagement surfaces 3250 contact the engagement members 3522, and the staple contact portions 3518 contact the top surface 3244 of the staple 3240 to position the staple 3240 in an open position for insertion into a bone. In the open position, the legs 3252, 3256 are moved laterally away from each other to an expanded position where the legs 3252, 3256 are positioned generally parallel to each other. The contact portions 3518 make contact with the top surface 3244 of the staple 3240 near a middle portion of the staple 3240 and the engagement members 3522 make contact with the ends of the staple 3240, positioning the staple 3240 to form an opening between the top surface 3244 of the staple 3240 and the recessed regions 3520 of the holder 3500. Thus, the staple insertion assembly has, for example, four points of contact between the staple 3240 and the holder 3500.

Referring now to FIGS. 30-39, an angled drill guide 4000 is shown. The angled drill guide 4000 includes a handle portion 4002 with a first end 4004 and a second end 4006. The drill guide 4000 includes a guide end 4008 at the first end 4004 and a staple engagement region 4018 at the second end 4006. The handle portion 4002 includes a tapered region 4010 near a mid-point of the drill guide 4000. The tapered region 4010 narrows the handle portion 4002 down to a guide end 4008. The guide end 4008 has a smaller width and height than the handle portion 4002 near the second end 4006. The handle portion 4002 for, for example, ergonomics purposes may also include, for example, at least one depression 4012 near a mid-point of the drill guide 4000 and at least one inset region 4014 positioned between the tapered region 4010 and the second end 4006. The handle portion 4002 may include, for example, two depressions 4012 and two inset regions 4014, one of each positioned on the top surface of the drill guide 4000 and the second of each positioned on the bottom surface of the drill guide 4000. In addition, the handle portion 4002 may include a plurality of ridges or recesses 4016 positioned along the sides of the drill guide 4000 between the tapered region 4010 and the second end 4006 for, for example, gripping purposes.

The drill guide 4000 may also include a staple engagement region 4018 positioned at the second end 4006, as shown in FIGS. 30 and 37-39. The staple engagement region 4018 may include a recessed region 4020 and at least one protrusion 4022 positioned adjacent to the recessed region 4020 to facilitate contact with a partially inserted staple. The recessed region 4020 may be, for example, generally "Y" shaped having three extension portions 4021, as shown in FIG. 39. The recessed region 4020 may be, for example, sized to receive the bridge portion 3132 of the staple 3130. The recessed region 4020 may be positioned on a staple 3130 with the first end 4004 of the drill guide 4000 being used as a contact point for a hammer or tamp to hit and fully insert the staple 3130 into the patient's bones or bone fragments The drill guide 4000 may further include a guide portion 4024 positioned at the first end 4004 and coupled to the guide end 4008, as shown in FIGS. 30-36. The guide portion 4024 may include a base 4026 with openings 4028 extending through the guide portion 4024 from a top surface to a bottom surface. The guide portion 4024 may also include a first guide member 4030 positioned on a first side of the drill guide 4000 and a second guide member 4040 positioned on a second side of the drill guide 4000, as shown in FIGS. 36-39. The first guide member 4030 may include a first end 4032 and a second end 4034. Each end of the first guide member 4030 may include a plurality of teeth 4036 for contacting or engaging a bone or bone fragment. The first guide member 4030 may also include a through hole or opening 4038 to facilitate the passage of a drill bit and/or guide pin or guidewire there through. The second guide member 4040 may include a first end 4042 and a second end 4044. Each end of the second guide member 4040 may include a plurality of teeth 4046 for engaging a bone or bone fragment. The second guide member 4040 may also include a through hole or opening 4048 sized to allow for the passage of a drill bit and/or guide pin or guidewire. The first guide member 4030 may have a length, for example, that is larger than the length of the second guide member 4040.

Referring now to FIGS. 40-47, a straight drill guide 4100 is shown. The straight drill guide 4100 includes a handle portion 4102 with a first end 4104 and a second end 4106. The drill guide 4100 includes a guide end 4108 at the first end 4104 and a tapered region 4110 at the second end 4106. The handle portion 4102 includes a tapered region 4110 positioned near a mid-point of the drill guide 4100. The tapered region 4110 narrows the handle portion 4102 down to a guide end 4108. The guide end 4108 having a smaller width and height than the handle portion 4102 near the second end 4106. The handle portion 4102 may also include, for example, at least one depression 4112 near a mid-point of the drill guide 4100 and at least one inset region 4114 positioned between the tapered region 4110 and the second end 4106. The handle portion 4102 may include, for example, two depressions 4112 and two inset regions 4114, one of each positioned on the top surface of the drill guide 4100 and the second of each positioned on the bottom surface of the drill guide 4100. The depressions 4112 facilitate user gripping of the handle portion 4102. In addition, the handle portion 4102 may include a plurality of ridges or recesses 4116 positioned along the sides of the drill guide 4100 between the tapered region 4110 and the second end 4106.

Figure 47:
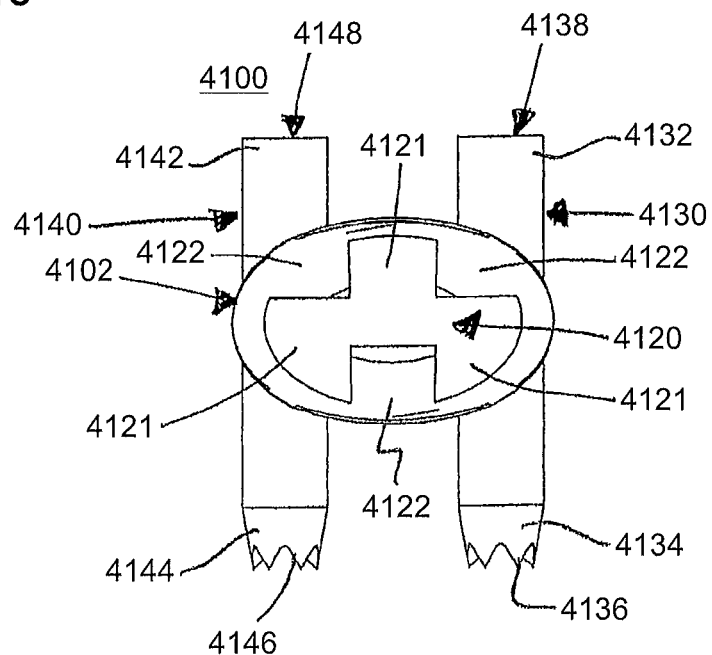
FIG. 47 is a second end view of the staple insertion instrument of FIG. 40, in accordance with an aspect of the present invention.

The drill guide 4100 may also include a staple engagement region 4118 positioned at the second end 4106, as shown in FIGS. 40 and 47. The staple engagement region 4118 may include a recessed region or notch 4120 and at least one protrusion 4122 positioned adjacent to the recessed region 4120. The recessed region 4120 may be, for example, generally "Y" shaped having three extension portions 4121, as shown in FIG. 47. The recessed region 4120 may be, for example, sized to contact or receive the bridge portion 3242 of the staple 3240. The recessed region 4120 may be positioned on a staple 3240 with the first end 4104 of the drill guide 4100 being used as a contact point for a hammer or tamp to hit and fully insert the staple 3240 into the patient's bones or bone fragments.

Figure 46:
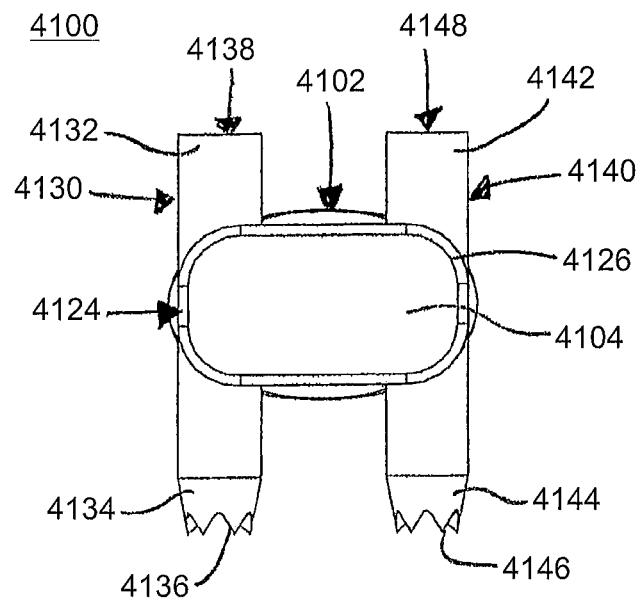
FIG. 46 is a first end view of the staple insertion instrument of FIG. 40, in accordance with an aspect of the present invention.

The drill guide 4100 may also include a guide portion 4124 positioned at the first end 4104, as shown in FIGS. 40-46. The guide portion 4124 may include a base 4126 with openings 4128 extending through the guide portion 4124 from a top surface to a bottom surface. The guide portion 4124 may also include a first guide member 4130 positioned on a first side of the drill guide 4100 and a second guide member 4140 positioned on a second side of the drill guide 4100, as shown in FIGS. 46-47. The first guide member 4130 may include a first end 4132 and a second end 4134. The second end 4134 of the first guide member 4130 may include a plurality of teeth 4136 for gripping or holding a bone or bone fragment. The first guide member 4130 may also include a through hole or opening 4138 that is sized to allow a drill bit (not shown) to pass through. The second guide member 4140 may include a first end 4142 and a second end 4144. The second end 4144 of the second guide member 4140 may include a plurality of teeth 4146 for contacting or engaging a bone or bone fragment. The second guide member 4140 may also include a through hole or opening 4148 for guiding an inserted drill bit (not shown). The first guide member 4130 may have a length, for example, that is equal to the length of the second guide member 4140.

A method of using a staple insertion assembly 3000, 3200 of FIGS. 1-2 and 15-16 or staple holder 3100, 3210, 3300, 3400, 3500 may include, for example, preparing the patient's bones or bone fragments and preparing the staple insertion assembly 3000, 3200 for use. Preparing the staple insertion assembly 3000, 3200 may include selecting the desired staple holder 3100, 3210, 3300, 3400, 3500 and staple 3130, 3240 and inserting the staple 3130, 3240 into the corresponding holder 3100, 3210, 3300, 3400, 3500. The staple 3130, 3240 may be positioned in the holder 3100, 3210, 3300, 3400, 3500 in an opened position as described in greater detail above, which will not be described again here for brevity sake. After the staple insertion assembly 3000, 3200 is selected and the bones or bone fragments are aligned, a drill guide 4000, 4100 may be selected which corresponds with the selected staple 3130, 3240 and holder 3100, 3210, 3300, 3400, 3500. The drill guide 4000, 4100 may be aligned with and positioned on the bones or bone fragments and a drill may be inserted through the two openings 4038, 4048, 4138, 4148 in the drill guide 4000, 4100 to form an opening in each bone or bone fragment. Each opening in the bone or bone fragment will receive a leg 3142, 3146, 3252, 3256 of the staple 3130, 3240. Next, the staple 3130, 3240 may be aligned with and inserted into the openings in the bones or bone fragments.

Once the staple 3130, 3240 is inserted into the desired position within the bones or bone fragments, the gripping portion 3106, 3216, 3306, 3406, 3506 of the holder 3100, 3210, 3300, 3400, 3500 may be angled, rotated or twisted to release the staple 3130, 3240 from the holder 3100, 3210, 3300, 3400, 3500. As the gripping portion 3106, 3216, 3306, 3406, 3506 is rotated each of the members 3124, 3126, 3234, 3236, 3336, 3338, 3340, 3436, 3438, 3440, 3524, 3526 of the holder 3100, 3210, 3300, 3400, 3500 adjacent to the slot 3110, 3220, 3328, 3332, 3428, 3432, 3510 will also rotate to disengage the four points of contact with the staple 3130, 3240. As the four points of contact disengage the staple 3130, 3240 is released from the receiving portion 3116, 3226, 3320, 3420, 3516 of the holder 3100, 3210, 3300, 3400, 3500. As the staple 3130, 3240 is released from the holder 3100, 3210, 3300, 3400, 3500, the legs 3142, 3146, 3252, 3256 of the staple 3130, 3240 will move to a closed position. The closed position of the staple 3130, 3240 will produce a compressive force between the bones or bone fragments, for example, at an osteotomy site and draw the opposing bones closer together. After the staple 3130, 3240 is inserted into the bone or bone fragments and released from the holder 3100, 3210, the surgical procedure may be completed and the patient's incision may be closed.

Many further modifications of the surgical staple and/or the instruments are also possible.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. A staple insertion assembly for inserting a staple into tissue, comprising:
a staple holder with a first end and a second end, comprising:
a gripping portion at the first end;
at least one slot extending from the second end toward the first end; and
a receiving portion at the second end, comprising:
at least one staple contact portion;
a first recessed region positioned adjacent to the at least one staple contact portion on a first side and a second recessed region positioned adjacent to the at least one staple contact portion on a second side; and a first engagement member positioned adjacent to the first recessed region and a second engagement member positioned adjacent to the second recessed region; and a staple separately formed from the staple holder and retained in the receiving portion, the staple having a bridge defining a longitudinal axis and a pair of legs coupled to the bridge, the longitudinal axis of the bridge intersecting the first and second engagement portions, wherein the staple holder can advance the staple into tissue such that the bridge seats into contact with the tissue while the staple is retained in the receiving portion, and then the staple can be released from the staple holder.

2. The staple insertion assembly of claim 1, wherein the gripping portion is wider than the receiving portion.

3. The staple insertion assembly of claim 1, wherein the at least one slot is a single slot.

4. The staple insertion assembly of claim 3, wherein the single slot is positioned between a first holder side and a second holder side of the staple holder.

5. The staple insertion assembly of claim 4, wherein the at least one staple contact portion comprises:

a first staple contact portion positioned adjacent to the single slot on the first holder side; and a second staple contact portion positioned adjacent to the single slot on the second holder side.

6. The staple insertion assembly of claim 5, wherein the first recessed region extends into the staple holder a first distance and the first staple contact portion extends into the staple holder a second distance, wherein the first distance is larger than the second distance; and wherein the second recessed region extends into the staple holder a first distance and the second staple contact portion extends into the staple holder a second distance, wherein the first distance is larger than the second distance.

7. The staple insertion assembly of claim 6, wherein the first engagement member is curved and extends out beneath the first recessed region and the second engagement member is curved and extends out beneath the second recessed region.

8. The staple insertion assembly of claim 1, wherein the at least one slot is two slots.

9. The staple insertion assembly of claim 8, wherein the two slots are positioned to separate the receiving portion into three members.

10. The staple insertion assembly of claim 9, wherein the at least one staple contact portion is one contact portion.

11. The staple insertion assembly of claim 10, wherein the one contact portion is positioned on a third center member of the three members.

12. The staple insertion assembly of claim 11, wherein the first recessed region is positioned on a first member of the three members, the first recessed region extends into the staple holder a first distance, the first staple contact portion extends into the staple holder a second distance, and the first distance is larger than the second distance; and wherein the second recessed region is positioned on a second member of the three members, the second recessed region extends into the staple holder a first distance, the second staple contact portion extends into the staple holder a second distance, and the first distance is larger than the second distance.

13. The staple insertion assembly of claim 12, wherein the first engagement member is curved and extends out beneath the first recessed region and the second engagement member is curved and extends out beneath the second recessed region.

14. The staple insertion assembly of claim 1, wherein the second end of the staple holder is angled between a first holder side and a second holder side.

15. The staple insertion assembly of claim 1, wherein the second end of the staple holder is linear between a first holder side and a second holder side.

16. The staple insertion assembly of claim 1, wherein the receiving portion extends through the staple holder from a front side to a back side.

17. A staple insertion assembly, comprising:

a staple having a bridge with a longitudinal axis and two legs, each of the two legs extending at a first angle relative to each other when the bridge is in an unstressed configuration, the bridge having first and second extensions that extend longitudinally along the longitudinal axis beyond the two legs, the bridge being elastically deformable into a stressed configuration in which the legs extend at a second angle relative to each other; and a staple holder comprising:

a first end and a second end, a manual gripping portion at the first end, a staple receiving portion holding the staple at the second end, the staple receiving portion comprising:

a first staple contact portion which bears against the bridge of the staple, a first engagement member positioned at a first lateral side of the receiving portion that engages a lower surface of the first extension of the bridge of the staple along the longitudinal axis of the bridge, and a first recessed region positioned between the first staple contact portion and the first engagement member that remains out of contact with the staple, and at least one slot extending from the second end toward the first end and into the staple receiving portion, wherein the first staple contact portion applies a first force at an upper surface of the bridge and the first engagement member applies an opposing second force at the lower surface of the bridge to hold the bridge in the stressed configuration.

18. The staple insertion assembly of claim 17, wherein the staple receiving portion further includes, a second staple contact portion which bears against the bridge of the staple, a second engagement member positioned at a second lateral side of the receiving portion that engages the second extension of the bridge of the staple, and a second recessed region positioned between the second staple contact portion and the second engagement member, the second recessed region remaining out of contact with the staple, wherein the at least one slot extends between the first and second engagement members.

19. The staple insertion assembly of claim 18, wherein the at least one slot extends between the first and second staple contact portions.

20. The staple insertion assembly of claim 18, wherein the at least one slot is a single slot that extends centrally between the first and second contact portions, centrally between the first and second recessed regions, and centrally between the first and second engagement members.

21. The staple insertion assembly of claim 18, wherein the staple holder is adapted to flex relative to the at least one slot.

22. The staple insertion assembly of claim 21, wherein the staple holder can be flexed to release the staple from the staple receiving portion of the staple holder.

23. A staple holder for retaining a staple having a bridge with a longitudinal axis and two axially opposed ends and two legs extending adjacent the ends of the bridge, comprising:
a gripping portion at a first end;
at least one slot extending from a second end toward the first end; and
a receiving portion opening at the second end opposite the first end, the receiving portion comprising:
at least one staple contact portion;
a first recessed region positioned adjacent to the at least one staple contact portion on a first side and a second recessed region positioned adjacent to the at least one staple contact portion on a second side; and
a first engagement member positioned adjacent to the first recessed region and a second engagement member positioned adjacent to the second recessed region such that the first and second engagement members are configured to extend about beyond the ends of the bridge of the staple to retain the staple in the receiving portion, the longitudinal axis of the bridge extending through the axially opposed ends and intersecting the first and second engagement members.

24. The staple holder of claim 23, wherein the receiving portion extends through the staple holder from a front side to a back side.

25. The staple holder of claim 24, wherein the at least one slot is one slot and the one slot is positioned centered between a first holder side and a second holder side of the staple holder.

26. The staple holder of claim 25, wherein the at least one staple contact portion comprises:
a first staple contact portion positioned adjacent to the one slot on the first holder side, wherein the first recessed region extends into the staple holder a first distance, the first staple contact portion extends into the staple holder a second distance, and the first distance is larger than the second distance; and
a second staple contact portion positioned adjacent to the one slot on the second holder side, wherein the second recessed region extends into the staple holder a first distance, the second staple contact portion extends into the staple holder a second distance, and the first distance is larger than the second distance.

27. A staple holder, comprising:
a gripping portion at a first end;
a first holder side and a second holder side;
a slot positioned between the first holder side and the second holder side and extending from a second end toward the first end; and
a receiving portion at the second end, the receiving portion extending through the staple holder from a front side to a back side, the receiving portion including,
at least one staple contact portion;
a first recessed region positioned adjacent to the at least one staple contact portion on a first side and a second recessed region positioned adjacent to the at least one staple contact portion on a second side; and
a first engagement member positioned adjacent to the first recessed region and a second engagement member positioned adjacent to the second recessed region,
wherein a first staple contact portion is positioned adjacent to the slot on the first holder side, wherein the first recessed region extends into the staple holder a first distance, the first staple contact portion extends into the staple holder a second distance, and the first distance is larger than the second distance; and
a second staple contact portion is positioned adjacent to the slot on the second holder side, wherein the second recessed region extends into the staple holder a first distance, the second staple contact portion extends into the staple holder a second distance, and the first distance is larger than the second distance.

28. The staple holder of claim 27, wherein the first engagement member is curved and extends out beneath the first recessed region and the second engagement member is curved and extends out beneath the second recessed region.

29. A staple insertion assembly, comprising:
the staple holder of claim 27; and
a staple releasably retained in the receiving portion.

30. A staple insertion assembly, comprising:
a staple holder with a first end and a second end, the staple holder consisting of a unitary sheet of flat material, the staple holder comprising:
a gripping portion at the first end; and
a receiving portion at the second end, comprising:
at least one staple contact portion; and
opposed recessed regions on opposite sides of the at least one staple contact portion; and
a staple separately formed from the staple holder, the staple having
a bridge with oppositely extending first and second ends, and
first and second legs descending from the bridge, each of the first and second legs having a proximal end and a distal end, the proximal end intersecting the bridge and the distal end a free end, the first and second ends of the bridge protruding beyond the proximal ends of the first and second legs,
the first and second ends of the bridge received and retained in the opposed recessed regions of the receiving portion, and the at least one staple contact portion in contact with the bridge to retain the bridge in a deformed configuration.

31. The staple insertion assembly according to claim 30, wherein the staple holder further includes at least one slot extending from the second end toward the first end.

32. The staple insertion assembly according to claim 30, wherein the opposed recessed regions includes a first recessed region and a second recessed region, and the staple holder further includes a first engagement member positioned adjacent to the first recessed region and a second engagement member positioned adjacent to the second recessed region.

* * * * *